United States Patent
Collier et al.

(10) Patent No.: US 9,057,085 B2
(45) Date of Patent: *Jun. 16, 2015

(54) LOV-D ACYLTRANSFERASE MEDIATED ACYLATION

(75) Inventors: Steven J. Collier, Singapore (SG); Ee Ling Teo, Singapore (SG); Joly Sukumaran, Singapore (SG); Robert J. Wilson, Singapore (SG); Junye Xu, Singapore (SG)

(73) Assignee: Codexis, Inc., Redwood City, CA (US)

( * ) Notice: Subject to any disclaimer, the term of this patent is extended or adjusted under 35 U.S.C. 154(b) by 549 days.

This patent is subject to a terminal disclaimer.

(21) Appl. No.: 13/499,364

(22) PCT Filed: Sep. 24, 2010

(86) PCT No.: PCT/US2010/050253
§ 371 (c)(1),
(2), (4) Date: Jun. 11, 2012

(87) PCT Pub. No.: WO2011/041233
PCT Pub. Date: Apr. 7, 2011

(65) Prior Publication Data
US 2012/0244582 A1    Sep. 27, 2012

Related U.S. Application Data

(60) Provisional application No. 61/247,274, filed on Sep. 30, 2009, provisional application No. 61/247,253, filed on Sep. 30, 2009.

(51) Int. Cl.
| | |
|---|---|
| *C12P 21/06* | (2006.01) |
| *C12N 9/10* | (2006.01) |
| *C12P 17/06* | (2006.01) |
| *C07K 14/00* | (2006.01) |
| *C12P 7/62* | (2006.01) |

(52) U.S. Cl.
CPC .................. *C12P 17/06* (2013.01); *C07K 14/00* (2013.01); *C12N 9/1029* (2013.01); *C12N 9/1025* (2013.01); *C12P 7/62* (2013.01)

(58) Field of Classification Search
CPC ......... C12P 17/06; C12P 7/62; C12N 9/1029; C12N 9/1025
USPC .................................................. 435/125, 193
See application file for complete search history.

(56) References Cited

U.S. PATENT DOCUMENTS

| | | |
|---|---|---|
| 4,444,784 A | 4/1984 | Hoffman et al. |
| 4,582,915 A | 4/1986 | Sleteinger et al. |
| 4,820,850 A | 4/1989 | Verhoeven et al. |
| 5,393,893 A | 2/1995 | Kubela et al. |
| 5,458,848 A | 10/1995 | Burgaud et al. |
| 5,763,646 A | 6/1998 | Kumar et al. |
| 5,917,058 A | 6/1999 | Kumar et al. |
| 6,391,583 B1 | 5/2002 | Hutchinson et al. |
| 2003/0208046 A1 | 11/2003 | Hunter et al. |
| 2009/0191602 A1 | 7/2009 | Tang et al. |

FOREIGN PATENT DOCUMENTS

| | | |
|---|---|---|
| WO | WO 94/26920 A1 | 11/1994 |
| WO | WO 99/45003 A1 | 9/1999 |
| WO | WO 00/37692 A1 | 6/2000 |
| WO | WO 2005/040107 A1 | 5/2005 |
| WO | WO 2007/139871 A2 | 12/2007 |

OTHER PUBLICATIONS

Alberts, A.W., et al., 1980 "Mevinolin: A highly potent competitive inhibitor of hydroxymethylglutaryl-coenzyme A reductase and a cholesterol-lowering agent," *Proc. Natl. Acad. Sci.* 77, 3957-3961.

Chan, J.K., et al. 1983, "Biosynthesis of Mevinolin. Spectral Assignment by Double-Quantum Coherence NMR after High Carbon-12 Incorporation ," *J. Am. Chem. Soc.* 105, 3334-3336.

Endo, A. 1980, "Monacolin-K, a new hypocholesterolemic agent that specifically inhibits 3-hydroxy-3-methylglutaryl coenzyme A reducatse" *J. Antibiot.* 33,334-336.

Gao, et al, 2009, "Directed Evolution and structural characterization of a simvastatin synthase," *Chem. & Biol.*, 16:1064-1074.

Schimmel T.G., et al., 1997, "Purification and Characterization of lovastatin esterase from clonostachys compactiuscula ," *Appl. Environ. Microbiol.* 63:1307-1311.

Xie, et al., 2006, "Biosynthesis of Lovastatin Analogs with a Broadly Specific Acyltransferase," *Chem. Biol.* 13:1161-1169.

Xie, et al., 2008, "Rational improvement of simvastatin synthase solubility in *Escherichla coli* to higher whole-cell biocatalystic activity," *Biotech and Bioengin.* 102:20-28.

Xie, et al., 2009, "Acyltransferase mediated polyketide release from a fungal megasynthase.," *J. Am. Chem. Soc.* 131:8388-8389.

Yoshizawa, Y., et al., 1994"Revision of the biosynthetic origin of oxygens in mevinolin (lovastatin), a hypocholerterolemic drug from *Aspergillus terreus* MF 4845," *J.Am.Chem. Soc.* , 116, 2693-2694.

International Search Report and Written Opinion to PCT/US2010/050253 mailed Mar. 7, 2012.

*Primary Examiner* — Tekchand Saidha
*Assistant Examiner* — Md Younus Meah
(74) *Attorney, Agent, or Firm* — Codexis, Inc.

(57) ABSTRACT

Methods for the improved acylation of chemical substrates using LovD acyltransferases, thioesters having acyl groups, and (i) thiol scavengers and/or (ii) precipitating agents are presented. An improved method for the production of simvastatin using (i) activated charcoal as a thiol scavenger and/or (ii) ammonium hydroxide as a precipitating agent is also presented.

29 Claims, 6 Drawing Sheets

LOV-D ACYLTRANSFERASE MEDIATED ACYLATION

1. CROSS REFERENCE TO RELATED APPLICATIONS

The present application is a national stage application filed under 35 USC §371 and claims priority of the international application PCT/US2010/0505253, filed Sep. 24, 2010, and U.S. provisional patent application 61/247,724, and 61/247,254 both filed Sep. 30, 2009, which are hereby incorporated by reference herein.

2. REFERENCE TO SEQUENCE LISTING

The Sequence Listing concurrently submitted herewith under 37 CFR §1.821 in a computer readable form (CRF) via EFS-Web as file name CX2-032.txt is incorporated herein by reference. The electronic copy of the Sequence Listing was created on Sep. 24, 2010, with a file size of 52 Kbytes.

3. BACKGROUND

The invention relates to a process for forming simvastatin or simvastatin precursors using improved LovD acyltransferase mediated acylations.

Enzymes are biomolecules which catalyze the conversion of a chemical substrate into a product and have been used in the chemical synthesis of valuable natural products and pharmaceuticals. Advantageously, enzymes can function to increase the rate of chemical conversion of a substrate to a product (by lowering the activation energy for the reaction) and to direct the placement of functional groups, i.e. regioselectively and/or stereoselectively placing functional groups onto a substrate. Enzyme activity can be affected by other molecules known as inhibitors. These inhibitors function to decrease enzyme activity and can severely limit the conversion or rate of conversion of a starting substrate into product.

One particular group of useful enzymes includes the transferases. Transferases are enzymes that catalyze the transfer of a functional group, for example, alkyl, acyl or phosphate groups, from a substrate (designated the donor and sometimes known as the coenzyme) to another substrate (designated the acceptor). The enzyme thereby catalyzes a reaction between chemical compounds that results in the loss of functionality from the donor and a gain in functionality on the acceptor. The subclass of acyltransferases has been used, among other things, to regioselectively acylate chemical substrates such as monacolin J to form simvastatin.

Simvastatin is a semisynthetic derivative of the natural product lovastatin, which can be isolated from the fermentation broth of *Aspergillus terreus*. Both lovastatin and simvastatin are cholesterol lowering drugs that substantially lower the risk of heart disease among adults. The gene cluster for lovastatin biosynthesis in *A. terreus* has been described previously, for example, in U.S. Pat. No. 6,391,583. Encoded in the gene cluster is a 46 kD protein known as LovD, which functions as an acyltransferase.

Once lovastatin is produced via fermentation in an *A. terreus* host, simvastatin can be produced from lovastatin via a semisynthetic route. After isolation and purification of lovastatin from the fermentation broth, a typical semisynthesis can proceed by hydrolysis of the 2-methylbutyrate side arm in the presence of base to yield the intermediate monacolin J. Monacolin J is the immediate precursor to simvastatin. Following hydrolysis, the free acid is lactonized, the free hydroxyl at C13 is protected, and the C8 alcohol is acylated to provide a protected analogue of simvastatin. Subsequent deprotection affords simvastatin. See, e.g., WO 2007/139871.

Enzymatic transformations using lipases and esterases have also been investigated as alternatives to chemical derivation. See, e.g., PCT WO 2005/040107, PCT WO 94/26920 and T. G. Schimmel, et. al. in *Appl. Environ. Microbiol.* (1997) 63:1307-1311. Enzymatic variants suffer from decreased throughput of substrate, high loading requirements, slow enzyme conversion rate or poor enzyme turnover. Therefore, an enzymatic method of producing simvastatin, such as by selective acylation of the C8 hydroxy of monacolin J, which provides good to high yield with minimum isolation steps, good enzyme turnover and conversion rate, and/or reasonable loading requirements is important towards the efficient synthesis of simvastatin and additional statin analogs.

Accordingly, there has been a long-felt need for an enzymatic process which overcomes one or more limitations of the prior art, thereby providing a method for the efficient and expedient acylation of chemical substrates such as lovastatin or monacolin J using acyltransferases.

4. SUMMARY

It has been surprisingly discovered that the LovD acyltransferase mediated acylation of simvastatin precursors is an equilibrium process and that this equilibrium process may be adjusted in one or more ways to result in higher conversion and/or rate of conversion of substrate to product.

It has also been surprisingly discovered that simvastatin may be precipitated as an insoluble salt in the acylation of a simvastatin precursor during a LovD acyltransferase mediated acylation reaction, and that this results in a shift of equilibrium, thereby providing higher conversion and/or rate of conversion of substrate to product.

It has been surprisingly discovered that LovD acyltransferase may be inhibited by thiol byproducts produced during the acylation of monacolin J hydroxy acid salt. More particularly, it has been discovered that whereas LovD acyltransferase can mediate the acylation of monacolin J hydroxy acid salt into the corresponding simvastatin acid in high yield, the reaction rate of conversion may be improved by preventing the inhibition of the LovD enzyme by thiol byproduct. Accordingly, the present disclosure is, in one or more embodiments, directed to a method of preventing the inhibition of the LovD acyltransferase enzyme by addition of thiol scavengers. See FIG. 1.

Advantageously, it has been found that addition of thiol scavengers such as activated charcoal improves the conversion rate of monacolin J substrate to its acylated analogue when thioester compounds comprising acyl moieties are used as co-substrates. The methods described herein overcome one or more limitations of the prior art and satisfy a long felt need for an efficient and expedient synthesis of simvastatin and simvastatin precursors using LovD acyltransferase enzymes.

The present disclosure, in one or more embodiments, also provides a method of producing simvastatin which overcomes the newly discovered inhibition of LovD acyltransferase by thiol byproducts and which shifts the equilibrium toward reaction product. It has been further discovered that addition of a thiol scavenger such as activated charcoal prevents or reduces enzyme inhibition. This results in an improved enzymatic conversion of substrate to a target compound and thereby provides an advantageous method for the production of simvastatin. In particular embodiments, methods and materials designed to take advantage of the improved enzymatic conversion process are described. More particularly, the present disclosure, in one or more embodiments, is directed to a method for the production of an enzymatically acylated chemical substrate (simvastatin or a simvastatin precursor), wherein a thiol scavenger is utilized to prevent inhibition of the acyltransferase enzyme. See FIG. 1 (illustrating an exemplary and generalized LovD acyltransferase reaction wherein thiol byproduct is sequestered).

In one or more embodiments, the method comprises the steps of combining a LovD acyltransferase enzyme in a reaction medium with (i) a thiol scavenger and/or (ii) a precipitating agent, a substrate comprising a free hydroxyl moiety, and a thioester comprising an acyl moiety. The acyltransferase mediates the donation of an acyl moiety from the thioester to the free hydroxyl moiety, thereby producing the target compound. While not intending to be bound by any theory of operation, in embodiments wherein a thiol scavenger is utilized, the thiol scavenger is believed to sequester (bind or otherwise inactivate) the resulting thiol byproduct. The thiol byproduct may act as an enzyme inhibitor of LovD, thereby reducing enzyme activity and conversion of the substrate to product. Enzyme inhibition may be a result of competitive binding of the inhibitor to the enzyme. Also, again while not intending to be bound by any theory of operation, in embodiments wherein a precipitating agent is utilized, it is believed that removal of product from the reaction medium by precipitation results in a favorable shifting of the reaction equilibrium. Removal of thiol byproduct may also provide a favorable shifting of the equilibrium.

Embodiments described herein also include methods for generating simvastatin with a minimum of chemical steps using an improved LovD acyltransferase reaction. Advantageously, the improved acyltransferase reaction can optionally be combined with additional chemical steps, such as in "one-pot" chemical synthesis methods, to provide a method of producing simvastatin from lovastatin without isolation and purification of the monacolin J intermediate. For example, lovastatin may be hydrolyzed to monacolin J and the crude reaction product used as the substrate for the enzyme mediated acylation reaction. The present disclosure also provides methods and materials designed to take advantage of the improved LovD enzymatic process, such as that by which lovastatin is made, in order to produce related compounds such as the pravastatin derivative huvastatin.

Those of skill in the art will understand that the disclosure provided herein allows artisans to produce a wide variety of embodiments. In one exemplary embodiment, simvastatin is produced by combining together monacolin J or a monacolin J derivative (preferably monacolin J hydroxy acid), a thioester that donates an acyl moiety to the C8 hydroxyl group of monacolin J (or derivative) in the presence of a LovD acyltransferase, (i) a thiol scavenger (comprising, for example, activated charcoal) and/or (ii) a precipitating agent (such as ammonium hydroxide ($NH_4OH$)), and a LovD acyltransferase. The LovD acyltransferase functions to mediate the transfer of an acyl group from the thioester to regioselectively acylate the C8 hydroxyl group of monacolin J (or derivative), thereby producing simvastatin. The resulting byproduct thiol is sequestered (bound or deactivated by the thiol scavenger) when thiol scavenger is present. Reaction product is precipitated when a precipitating agent is present. Advantageously, reaction rate is noticeably or markedly improved.

A related embodiment provides a method of making simvastatin, comprising the steps of combining together lovastatin, a thioester that donates an acyl moiety to the C8 hydroxyl group of monacolin J in the presence of a LovD acyltransferase, (i) a thiol scavenger (comprising, for example, activated charcoal) and/or (ii) a precipitating agent (such as ammonium hydroxide ($NH_4OH$)) and a LovD acyltransferase. In this embodiment of the method, the LovD acyltransferase is allowed to hydrolyze lovastatin into monacolin J prior to the transfer of an acyl group from the thioester via a regioselective acylation of the C8 hydroxyl group of monacolin J using the acyltransferase, thereby providing simvastatin. The resulting byproduct thiol is sequestered (bound or deactivated by the thiol scavenger) when thiol scavenger is present. Reaction product is precipitated when a precipitating agent is present. Advantageously, reaction rate is improved and high conversions achieved.

The methods and materials described herein that are used to make simvastatin can be adapted to produce other compounds including those that are structurally similar to simvastatin, for example huvastatin. In this context, a method of making huvastatin is provided that comprises the steps of combining together hydrolyzed pravastatin tetra-ol, a thioester that donates an acyl moiety to the C8 hydroxyl group of hydrolyzed pravastatin tetra-ol in the presence of a LovD acyltransferase, (i) a thiol scavenger (comprising, for example, activated charcoal) and/or (ii) a precipitating agent (such as $NH_4OH$), and a LovD acyltransferase. The LovD acyltransferase is allowed to use an acyl group from the thioester to regioselectively acylate the C8 hydroxyl group of hydrolyzed pravastatin tetraol, so that huvastatin is made. The thiol scavenger (when present) is believed to again act by sequestering the thiol byproduct, thereby preventing inhibition of the LovD enzyme, resulting in an improved enzyme reaction rate and a shifting of the equilibrium towards reaction product. The precipitating agent (when present) is believed to shift the equilibrium toward reaction product by removing reaction product from solution. In yet another embodiment, huvastatin can be made directly from pravastatin. Pravastatin is combined with the LovD acyltransferase to hydrolyze pravastatin to the intermediate hydrolyzed pravastatin tetra-ol. Acylation by the LovD acyltransferase then can proceed upon addition of (i) a thiol scavenger and/or (ii) a precipitating agent, and a thioester comprising an acyl moiety.

In typical embodiments of the various methods described herein, the functional group donor is an acyl donor. Thioesters are one highly preferred group of donor compounds that can donate an acyl moiety to a chemical substrate in the presence of a LovD acyltransferase and a scavenging compound(s). For example, the C8 hydroxyl group of monacolin J may be acylated by a thioester in the presence of a LovD acyltransferase. A variety of such thioesters are disclosed herein. See, e.g., FIG. 4 (illustrating some preferred thioester compounds). In addition to the preferred thioesters of FIG. 4, other preferred thioesters include butyryl-thioesters, N-acetylcysteamine thioesters or methylthioglycolate thioesters. Biologically derived thioester compounds such as acetyl coenzyme A (Acetyl CoA) may be used in one or more embodiments. Acetyl CoA comprises a thioester between coenzyme A (a thiol) and acetic acid (an acyl group carrier). Accordingly, other compounds comprising acyl donors include acyl-CoA, butyrlyl-CoA, benzoyl-CoA, acetoacetyl CoA, D-hydroxybutyryl-CoA, malonyl-CoA and palmitoyal-CoA. The thioester group may comprise one or more functional groups such as, for example, an alkyl linker chain, an alkyl group(s), aryl group(s), esters, amides, sulfonates, phosphates, and so on. Preferably, the thioester comprises a short alkyl chain terminated in an ester or amide, or the thioester may comprise only an alkyl chain. Other functional group donors with the capacity to donate an acyl group are also contemplated as suitable donors. Other acyl donating groups which form thiol byproducts upon LovD-mediated acylation of the target substrate would benefit from the methods of one or more embodiments of the present disclosure, in particular, the addition of scavengers which sequester one or more thiol moieties, and/or the addition of precipitating agents.

Optionally, the thioester comprises one or more short ($C_1$-$C_2$), medium ($C_3$-$C_6$), or long ($>C_7$) chain length acyl group moieties which may be branched, unbranched, or cyclic. It is contemplated that in some instances the acyl group moieties may be functionalized. Some representative thioesters are α-dimethylbutyryl-5-methyl-mercaptopropionate (also known as methyl 3-(2,2-dimethylbutanoylthio)propanoate, DMB-S-MMP), dimethylbutyryl-5-ethyl mercaptopropionate (DMB-S-EMP), dimethylbutyryl-5-methyl thioglycolate (DMB-S-MTG) and dimethylbutyryl-5-methyl mercaptobutyrate (DMB-S-MMB). In an illustrative and preferred embodiment, the thioester is S-2-acetamidoethyl 2,2-dimethylbutanethioate, S-acetamidomethyl 2,2-dimethylbutanethioate, methyl 2-(2,2-dimethylbutanoylthio)acetate and/or methyl 3-(2,2-dimethylbutanoylthio)propanoate. Thioesters may be made by methods known in the art. In an exemplary process, the highly preferred thioester DMB-S-MMP may be prepared by acylation of methyl 3-mercaptopropanoate with 2,2-dimethylbutanoyl chloride in the presence of N,N-diisopropylethylamine (DIPEA). Other acyl thioesters may be made by utilizing other acyl chlorides (or halides) and inorganic or organic bases in the acylation of methyl 3-mercaptopropanoate.

Acyltransferase enzymes useful in the methods described herein are LovD acyltransferases. The LovD acyltransferase may be a wild-type LovD enzyme obtainable from *A. terreus*, or a mutant thereof, such as for example, the mutants described in Biotechnol Bioeng, 2009 Jan 1; 102(1):20-8. Specific exemplary LovD acyltransferases that catalyze the methods described herein with greatly increased reaction rates and yield as compared to wild-type LovD acyltransferase from *A. terreus* that can be advantageously used in the methods described herein are described in Application No. 61/247,253, titled "LovD Variants and Their Uses," filed Sep. 30, 2009 and application Ser. No. 12/890,134 filed Sep. 24, 2010. Suitable LovD acyltransferases are also described below in Section 6 (See, for example, Table 2).

The methods disclosed herein utilize one or more scavenger compounds or agents. Scavenger compounds adapted to scavenge thiol compounds include, for example, activated charcoal, isatoic anhydride, fluorous 2,4-dichloro-1,3,5-triazines (F-DCTs), vinyl ethers, dihydropyran, N-ethylmaleimide, p-(chloromercuri)benzoate, copper ions, and variants thereof. Thiol scavengers may be adapted by incorporation onto a solid-support and may be used alone or in combination with other scavengers including non-thiol scavengers, i.e. scavengers which act to bind or deactivate other functional groups which inhibit enzyme activity. In a preferred embodiment, activated charcoal is utilized.

The methods disclosed herein may also utilize in addition to or in exclusion to one or more scavenger compounds or agents, one or more precipitating agents. Preferred precipitating agents are compounds which function to donate a counterion to the acylated substrate which render the compound insoluble in the reaction medium. For example, ammonium hydroxide functions to donate an ammonium counterion ($NH_4^+$).

In certain embodiments described herein, the methods result in improved LovD enzyme activity. Improved enzyme activity corresponds to improved enzyme stability, improved enzyme rate, i.e. the rate at which substrate is modified, e.g., acylated, and/or improved enzyme loading requirements, e.g., the amount of enzyme required to achieve a given conversion in a given timeframe. In an exemplary and preferred embodiment, the enzyme rate is improved. For example, the rate at which acylation of monacolin J hydroxy acid, sodium salt to the corresponding simvastatin hydroxy acid, sodium salt is effected can be improved, i.e. complete equilibrium conversion, meaning the time at which no more substrate is acylated, occurs in less time as exemplified in the examples given below.

Certain embodiments of the methods for making simvastatin and related compounds using the improved LovD acyltransferase reaction may include further steps to purify these compounds. For example, embodiments of the disclosure can include at least one purification step comprising lysis of cells of an isolated organism present in the combination. Embodiments can also include at least one purification step comprising centrifugation of cells or cell lysates of an isolated organism present in the combination. Moreover, embodiments can include at least one purification step comprising precipitation of one or more compounds present in the combination. One embodiment of a precipitation step comprises the precipitation of a free acid form of simvastatin. Optionally in such embodiments, one can then convert this free acid form of simvastatin to a simvastatin salt. Embodiments of the disclosure can also include at least one purification step comprising filtration or chromatography of one or more compounds present in the combination. In addition, embodiments can include at least one analysis step comprising spectrometry such as proton or carbon NMR or chromatography such as flash chromatography, thin-layer chromatography, gas chromatography, and/or high performance liquid chromatography (HPLC).

Additional embodiments are discussed below.

5. BRIEF DESCRIPTION OF THE FIGURES

FIG. 1 provides a generalized scheme of the LovD acyltransferase mediated acylation of a hydroxyl group by a donor compound and subsequent "scavenging" of the thiol byproduct;

6. DETAILED DESCRIPTION

The LovD acyltransferase mediated acylation of statin precursors such as monacolin J or analogues and derivatives thereof is an equilibrium process. This means that reaction products may inhibit the additional formation of product. The equilibrium process can be shifted toward reaction product by either (i) increasing thioester loading; (ii) removing/sequestering thiol byproduct; or (iii) product precipitation. The processes of the present disclosure utilize one or more equilibrium shifting techniques to improve the percent conversion of substrate to product and/or the reaction rate. For example, in some embodiments, increased thioester loading is utilized to improve reaction yield/rate. In other embodiments, thiol byproduct is scavenged to improve reaction yield/rate. In yet other embodiments, product is precipitated during reaction, thereby improving reaction yield/rate. Equilibrium shifting techniques may be used in combination. For example, in some embodiments, additional thioester co-substrate and product precipitation are utilized (with or without the addition of a thiol scavenger).

The present disclosure, in one or more embodiments, provides a novel process for the improved acylation of chemical substrates using LovD acyltransferase. Preferred embodiments include a method of improving the acyltransferase activity of LovD or its variants by addition of scavenger compound(s). Another preferred embodiment comprises the use of a precipitating agent. Yet additional preferred embodiments include a method of producing an acylated chemical substrate using LovD acyltransferase, a thioester comprising an acyl moiety and (i) a scavenging compound(s) and/or (ii) a precipitating agent. Exemplary of one or more preferred embodiments is an improved process for the acylation and hence production of simvastatin from either lovastatin or monacolin J (or its hydroxy acid salts) using the LovD acyltransferase, a thioester comprising an acyl moiety, and (i) a scavenging compound(s) and/or (ii) a precipitating agent.

One exemplary and preferred scavenger compound is activated charcoal. Without being tied to any one theory of operation, it is hypothesized that activated charcoal traps LovD enzyme inhibiting thiol byproducts and/or converts ("deactivates") thiol byproducts into disulfides that do not interfere with enzyme activity. Other thiol scavengers which do not interfere with enzyme activity and which bind or deactivate thiol byproducts are also preferred.

6.1. Definitions

Figure 5:
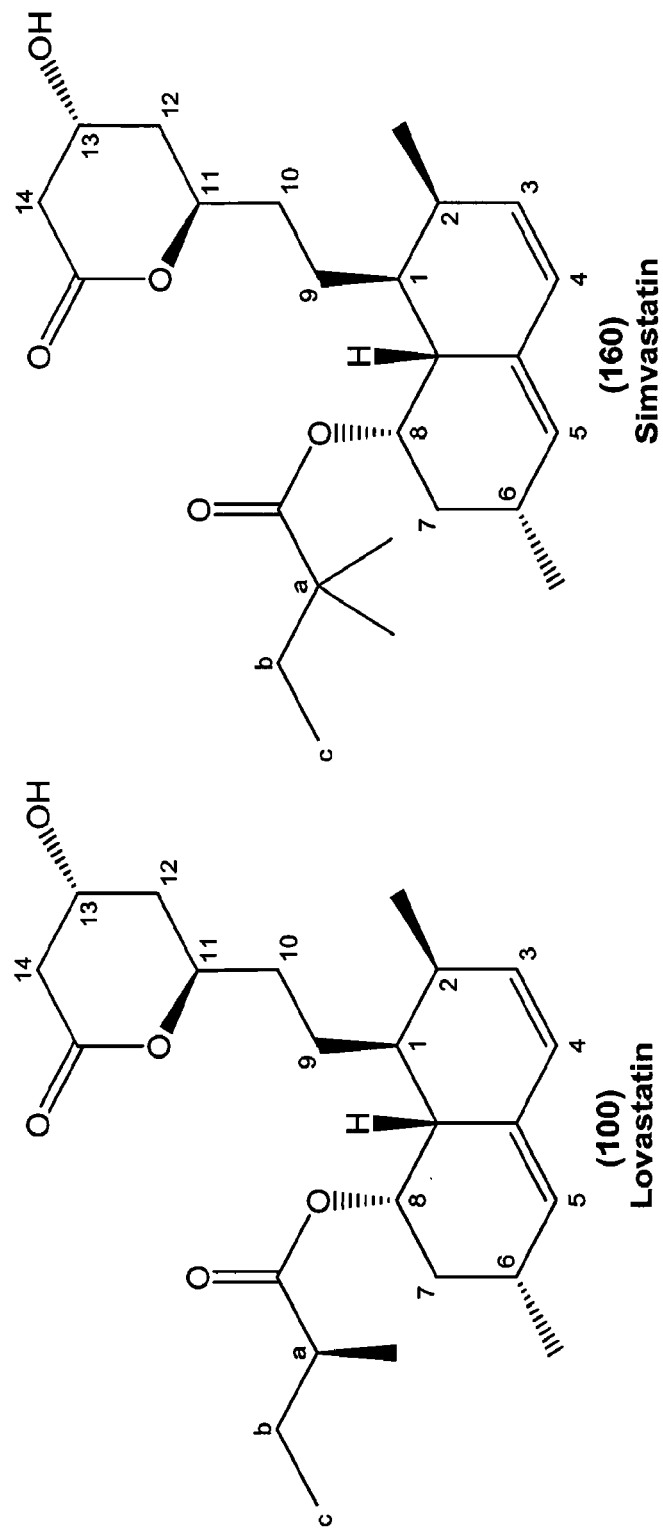
FIG. 5 illustrates lovastatin (100) and simvastatin (160) with chemical numbering and labels.

As used herein, the following terms are intended to have the following meanings:

"Lovastatin" (Mevacor®) is a fungal polyketide produced by *Aspergillus terreus*. See, e.g., A. W. Alberts, J. et. al., *Proc. Natl. Acad. Sci. U.S.A.*, 1980, 77, 3957-3961 and A. Endo, *J. Antibiot.* 1980, 33, 334-336; and J. K. Chan, et. al., *J. Am. Chem. Soc.* 1983, 105, 3334-3336; Y. Yoshizawa, et. al., *J. Am. Chem. Soc.* 1994, 116, 2693-2694. It is a pharmaceutically important compound because of its potent inhibitory activities towards hydroxymethylglutaryl coenzyme A reductase (HMGR), the rate-limiting step of cholesterol biosynthesis, and therefore it is widely used in the treatment of hyperlipidemia, hypercholesterolemia, and the like. See FIG. 5 for chemical numbering and labeling of lovastatin (100).

"Simvastatin" is an analog of lovastatin. It is favored over lovastatin because of the absence of adverse side effects and its high absorbability in the stomach. Also, it has been reported that simvastatin prevents and reduces the risk of Alzheimer's disease (AD) by retarding the production of Ab42, a β-amyloid protein associated with AD. It is known in the art that simvastatin can be synthetically prepared. See, e.g., U.S. Pat. Nos. 4,444,784, 4,582,915, 5,393,893, 5,763, 646 and 5,763,653, EP Pat. No. 299,656 and Intl. Pat. Pub. No. WO 99/45003. See FIG. 5 for chemical numbering and labeling of simvastatin (160).

"Lovastatin derivatives" as used herein comprises lovastatin derivatives or precursors, for example: pravastatin, huvastatin, and simvastatin.

"Monacolin J variants" refers to monacolin J variants disclosed in the art, for example, the hydrolyzed pravastatin tetra-ol or 6-hydroxy-6-desmethylmonacolin J and the like. In certain embodiments of the disclosure, "monacolin J variants" refers to monacolin J compounds having substitutions at the C6 position or to the hydroxy acid form of monacolin J (and salts thereof).

Skilled artisans will appreciate that lovastatin, monacolin J and simvastatin, as well as their analogues and derivatives can exist in various forms including acid, ester, amide and lactone forms. The acid, ester, amide and lactone forms can also be in the form of salts. The acid (R=—OH), ester (R=—O(alkyl)), amide (R=—N(alkyl)$_2$) and lactone forms of these compounds are illustrated below. Unless stated otherwise, "lovastatin" as used herein includes the acid, ester, amide, lactone and salt forms, "monacolin J" as used herein includes the acid, ester, amide, lactone and salt forms and "simvastatin" as used herein includes the acid, ester, amide, lactone and salt forms. These forms can be used in the methods described herein.

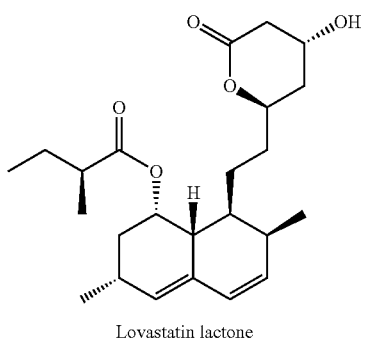

Lovastatin lactone

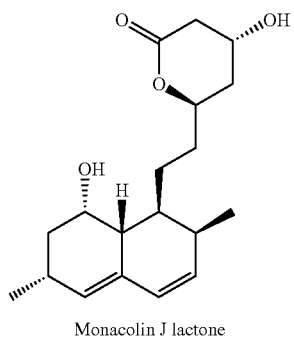

Monacolin J lactone

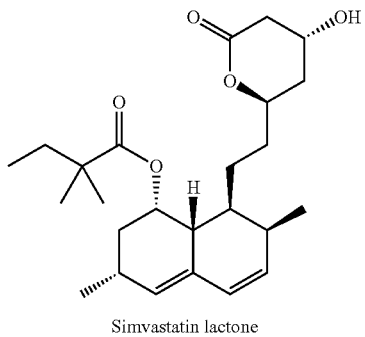

Simvastatin lactone

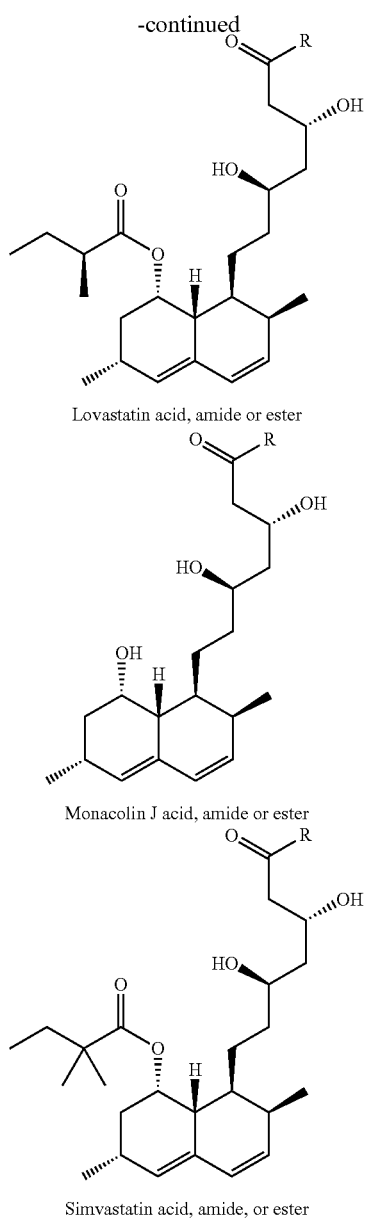

Lovastatin acid, amide or ester

Monacolin J acid, amide or ester

Simvastatin acid, amide, or ester

The salts of these compounds (e.g., pharmaceutically acceptable salts known in the art) can occur both as a free acid as well as a sodium, potassium, ammonium, or other salts derived from metals of group I or group II including alkaline earth elements or other metallic salts. Organic salts may also be utilized including, for example, ammonium and triethanolamine salts. Such salts may be found in combination; for example, a simvastatin salt could be a combination of sodium and potassium salts with simvastatin.

"*Aspergillus terreus*" or "*A. terreus*" is a filamentous ascomycete commonly found in soil. A variety of *A. terreus* strains are known in the art, for example, those deposited as ATCC 20542 and ATCC 20541.

"LovD acyltransferase" as used herein refers to those polypeptides that can use a thioester to regiospecifically acylate the C8 hydroxyl group of monacolin J or 6-hydroxy-6-des-methyl monacolin J so as to produce simvastatin or huvastatin, respectively. See, e.g., Xie et al., 2006, "Biosynthesis of Lovastatin Analogs with a Broadly Specific Acyltransferase," Chem. Biol. 13:1161-1169. LovD acyltransferases include, by way of example and not limitation, the wild-type LovD acyltransferase obtainable from *A. terreus* (amino acid sequence provided herein as SEQ ID NO:2), as well as mutants, variants, and truncated forms thereof, as will described in more detail below).

As disclosed herein, an "acyl donor" or "acyl carrier" is a compound having an acyl group that can be transferred to a target substrate, such as, for example, simvastatin and/or a simvastatin precursor or a related compound. Typically, an "acyl donor" or "acyl carrier" is a thioester that donates (as mediated by an acyltransferase) an acyl moiety to a specific region on a target molecule, such as, for example, the C8 hydroxyl group of monacolin J. A wide variety of such agents are known in the art to have this activity. See, e.g., WO 2007/139871. In addition to those known in the art and further shown by the instant disclosure to have this activity, any potential acyl donor/carrier known in the art (or synthesized de novo) having an ability to acylate a target substrate via an acyltransferase, such as C8 of monacolin J (thereby producing simvastatin), can be easily identified by comparative experiments with the acyl donors disclosed.

Other examples of acyl donors include, but are not limited to, α-dimethylbutyryl-SNAC, acyl-thioesters, acyl-CoA, butyryl-CoA, benzoyl-CoA, acetoacetyl-CoA, β-hydroxybutyryl-CoA, malonyl-CoA, palmitoyal-CoA, butyryl-thioesters, N-acetylcysteamine thioesters (SNAC), methyl-thioglycolate (SMTG), benzoyl-SNAC, benzoyl-SMTG or α-S-methylbutyryl-SNAC. These compounds can be produced naturally or synthetically, and, in some cases, can penetrate a cell membrane. A number of these compounds can be added to a reaction medium comprising LovD and monacolin J to produce simvastatin, for example.

"Acyl-SNAC" as used herein refers to α-dimethylbutyryl-SNAC. As is known in the art, acyl-SNAC can penetrate a cell membrane under in vivo conditions. LovD can use acyl-SNAC as a substrate to initiate the reaction from monacolin J to simvastatin by regiospecifically acylating the C8 hydroxyl group of monacolin J. Acyl-SNAC can donate its acyl group to LovD.

"Alkyl" means an unsubstituted or substituted alkyl group. An alkyl can be, for example, cyclic, acyclic, branched, or linear.

"Aryl" means an unsubstituted or substituted aryl group and may comprise heterocycles.

"A thioester comprising an acyl moiety" means a thioester having an acyl moiety which undergoes a mediated transfer to a substrate when treated under appropriate conditions with an acyltransferase. For example, a compound of general formula R—C(=O)—SR' wherein R is an alkyl or aryl and R' is variable comprises an acyl group as R—C(=O)—.

"A suitable reaction medium" is a solvent system, mono or biphasic, which allows the components of the reaction mixture to combine and produce product. Exemplary reaction mediums include ether, ethyl acetate, hexanes, tetrahydrofuran, methanol, isopropanol, acetone, dimethylformamide, dichloromethane, chloroform, tert-butyl methyl ether (MTBE), water, acetonitrile, and combinations thereof. Reaction mediums may be buffered to maintain a specific pH or pH range such as by addition of acids, bases, or salts. For example, one exemplary reaction medium is a triethanolamine buffered aqueous suspension of reactants. Another exemplary reaction medium is ethyl acetate with the addition of methanol. Preferably, reaction mediums are maintained at controlled temperatures, under inert atmospheres such as argon or nitrogen, and with mechanical or magnetic stirring.

A "scavenger compound" is a compound which binds, chemical modifies to an inert form (relative to enzyme activity) or removes a byproduct formed during an acyltransferase mediated acylation reaction. The process of binding or chemically modifying a compound to an inert form is also known as sequestering.

"Activated charcoal," also called activated carbon or activated coal, is a form of carbon that has been processed to provide a very large surface area. A suitable form of activated charcoal is represented by Fluka® puriss.p.a. powdered activated charcoal (CAS No. 7440-44-0, iodine-adsorption (0.05 mol $I_2$/l) of >70 mL/g).

LovD "Acyltransferase mediated acylation" means acylation of a substrate is mediated by the LovD acyltransferase. Without being bound by any one theory of operation, it is believed that LovD acyltransferase is acylated by a thioester compound, accepting the acyl-moiety of the thioester and producing a thiol byproduct. Subsequently, a free hydroxyl may then accept the acyl-moiety attached to the LovD acyltransferase, thereby becoming acylated itself and regenerating the active LovD acyltransferase. It has been discovered that the production of thiol compounds during the acyltransferase reaction results in decreased activity of the enzyme. In particular, it has been found that thiol compounds inhibit the rate of enzyme conversion of substrate to target.

"Precipitating agent" is a chemical agent which induces the precipitation of a compound or which converts a starting material into a compound which becomes insoluble after subsequent reaction. Precipitation is understood to mean the deposition of insoluble matter in a reaction medium, i.e. the formation of a solid in a solution during a chemical reaction. A precipitation agent functions by converting a normally soluble compound into a compound which undergoes precipitation in the reaction medium or which undergoes precipitation in the reaction medium upon further conversion to a target. A precipitating agent may also function to maintain or adjust solution pH. For example, ammonium hydroxide may be utilized as a precipitating agent in that monacolin J hydroxy acid may be converted to its ammonium salt prior to acylation. Acylation in a suitable reaction medium then results in an insoluble product. Ammonium hydroxide also functions to adjust the pH of the solution.

"Insoluble," "Substantially Insoluble," and "Partially Insoluble" refer to the ability of a solute to form a solution in a liquid solvent. Solubility is, unless otherwise stated, measured at room temperature and pressure. A substance is insoluble if for a given solvent system, i.e. a medium comprising one or more solvents, complete dissolution under reaction concentrations is not achievable. A substance is substantially insoluble if no more than 5% of the substance undergoes dissolution under reaction concentrations in a given solvent system. A substance is partially insoluble if more than 5% but less than 95% of the substance undergoes dissolution under reaction concentrations in a given system. A precipitating agent achieves at least the partial insolubility of a compound.

6.2. Detailed Description

Figure 1:
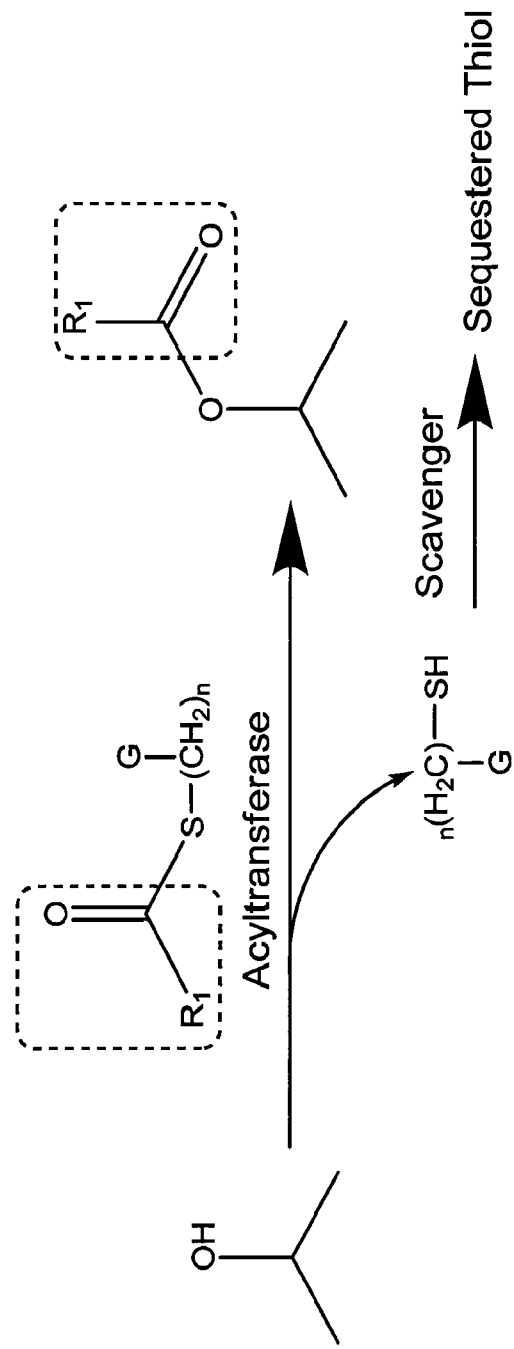

The present disclosure, in one or more embodiments, provides methods and materials designed to take advantage of an improved LovD acyltransferase reaction. More particularly, one or more embodiments provide a method for the production of a LovD acylated chemical substrate, wherein a thiol scavenger is utilized to prevent inhibition of the LovD acyltransferase enzyme. See FIG. 1. In a typical embodiment, the method comprises the steps of combining LovD acyltransferase enzyme in a reaction medium comprising a thiol scavenger, a substrate comprising a free hydroxyl moiety and a thioester. LovD mediates the donation of an acyl moiety from the thioester to the free hydroxyl moiety, thereby producing the target compound. The thiol scavenger sequesters or otherwise inactivates the resulting thiol byproduct, which is believed to act as an enzyme inhibitor, thereby allowing improved enzymatic conversion of the substrate to product.

In other embodiments, a method for the production of a LovD acylated chemical substrate, wherein a precipitating agent is utilized which renders the final product insoluble in the reaction medium, is disclosed. In a typical embodiment, the method comprises the steps of combining LovD acyltransferase enzyme in a reaction medium comprising a precipitating agent, a substrate comprising a free hydroxyl moiety and a thioester. LovD mediates the donation of an acyl moiety from the thioester to the free hydroxyl moiety, thereby producing the target compound. The target compound is rendered insoluble as a result of the precipitating agent. Removal of the target compound by precipitation results in a favorable shift in the equilibrium of the reaction.

The present disclosure also provides, in one or more embodiments, a method of acylating a chemical substrate comprising a free hydroxyl compound using LovD acyltransferase, (i) a thiol scavenger and/or (ii) a precipitating agent, and a compound of general formula (I):

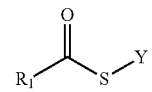

wherein:
R$_1$ represents an aryl or alkyl group; and
Y is (a) —(CH$_2$)$_n$—NR$_2$—(CO)—R$_3$; or (b) —(CH$_2$)$_n$—(CO)O—R$_3$; or (c) —(CH$_2$)$_n$—H or an optionally substituted alkyl or optionally substituted aryl group;
wherein n is an integer from 1-10 and R$_2$ and R$_3$ are, independently, an alkyl or aryl group.

The method comprises combining the free hydroxyl containing compound into a suitable reaction medium with the LovD acyltransferase, (i) a thiol scavenger and/or (ii) a precipitating agent, and a thioester comprising an acyl moiety. For example, the free hydroxy containing compound can be added into a round bottom flask comprising a suitable reaction medium, such as an aqueous solution buffered to within pH 6-11 and often pH 7-10 by addition of a base, e.g., triethanolamine, ammonium hydroxide, sodium hydroxide, or other inorganic or organic bases. Under stirring, the reaction vessel can be charged with the LovD acyltransferase enzyme, (i) a thiol scavenger and/or (ii) a precipitating agent and then the thioester. The reaction can be monitored to follow conversion of the substrate, such as by HPLC, thin-layer chromatography, or other suitable methods. As appropriate, additional enzyme or other reactant (e.g., thioester) may be added to effect optimal conversion. Workup, such as by appropriate quenching when necessary, and extraction of the target compound or direct filtration of the product may be effected when the desired conversion has been achieved. Filtration, such as through Celite® and drying of organic extracts, such as by addition of sodium sulfate or magnesium sulfate or by azeotropic drying, may also be performed. Extracts containing the product may be concentrated by appropriate methods such as under reduced pressure.

The present disclosure also provides, in one or more embodiments, a method of acylating a chemical substrate comprising a free hydroxyl compound using LovD acyltransferase, (i) a thiol scavenger and/or (ii) a precipitating agent and a compound of general formula (II):

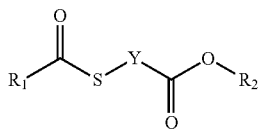

wherein:
R$_1$ and R$_2$ represent, independently, an aryl or alkyl group; and
Y is —(CH$_2$)$_n$— or an optionally substituted alkyl or optionally substituted aryl group;
wherein n is an integer from 1-10.

The method comprises combining the free hydroxyl containing compound into a suitable reaction medium with the LovD acyltransferase, (i) a thiol scavenger and/or (ii) a precipitating agent and a thioester comprising an acyl moiety. The chemical substrate can be lovastatin, monacolin J (or its hydroxy acids or hydroxy acid salts) or analogues thereof comprising a free hydroxyl group. The present disclosure also provides, in one or more embodiments, a method of acylating a chemical substrate comprising a free hydroxyl compound using LovD acyltransferase, (i) a thiol scavenger and/or (ii) a precipitating agent and a compound of general formula (III):

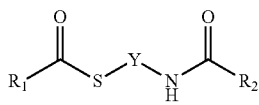

wherein:
R$_1$ and R$_2$ represent, independently, an aryl or alkyl group; and
Y is —(CH$_2$)$_n$— or an optionally substituted alkyl or optionally substituted aryl group;
wherein n is an integer from 1-10.

The method comprises combining the free hydroxyl containing compound into a suitable reaction medium with LovD acyltransferase, (i) a thiol scavenger and/or (ii) a precipitating agent and a thioester comprising an acyl moiety. The chemical substrate can include lovastatin, monacolin J (or its hydroxy acids or hydroxy acid salts) and analogues thereof comprising a free hydroxyl group. The present disclosure also provides, in one or more embodiments, a method of acylating a chemical substrate comprising a free hydroxyl compound using LovD acyltransferase, (i) a thiol scavenger and/or (ii) a precipitating agent and a compound of formula (IV):

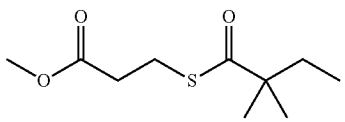

The present disclosure comprises, in one or more embodiments, a method of acylating lovastatin or monacolin J (or its hydroxy acids or hydroxy acid salts) and analogues thereof using LovD acyltransferase, (i) a thiol scavenger comprising activated charcoal and/or (ii) a precipitating agent comprising ammonium hydroxide, and a compound of formula (IV), comprising combination of the reactants in a suitable reaction medium, thereby allowing LovD to produce acylated forms of lovastatin or monacolin J.

As shown in table 1, thioesters as used in the present disclosure have relative rates of reactivity, meaning some thioester compounds increase reaction rate. Any one or more compounds shown in Table 1 may be used as thioesters in the methods of the present disclosure. Compound IV is one preferred thioester as its relative activity is high.

TABLE 1

| Compound | Structure | Relative activity at 24 h (%) |
|---|---|---|
| IV | 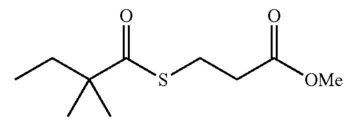 | ++++ |
| V | 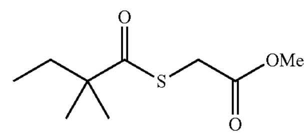 | ++ |
| VI | 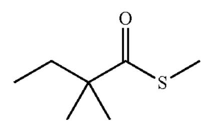 | + |
| VII | 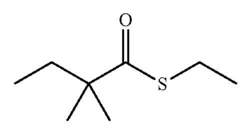 | ++ |
| VIII | 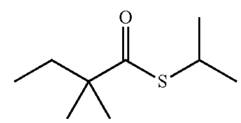 | + |
| IX | 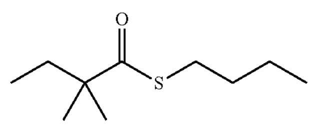 | +++ |

+ = 0-1
++ = 1-10
+++ = 10-75
++++ = 75-100

The present disclosure also provides, in one or more embodiments, a method of improving the enzymatic activity of LovD. The method comprises the addition of (i) a scavenger, preferably a thiol scavenger, and most preferably activated charcoal and/or (ii) a precipitating agent, preferably an agent which renders the product substantially insoluble, and more preferably ammonium hydroxide. In an exemplary embodiment, monacolin J hydroxy acid, sodium salt is acylated using a LovD or LovD variant enzyme using a thioester in the presence of activated charcoal. In yet another exemplary embodiment, a reaction medium is charged with 75 g/L of monacolin J hydroxy acid, sodium salt, 1.5 g/L of enzyme (LovD or equivalent amount of LovD variant), 1.7 equivalents (relative to the substrate) of thioester, and 10 g/L of activated charcoal. The reaction may be run using a 200 mM triethanolamine buffer at pH 9.0 at room temperature. In the exemplary example, >98% of substrate is converted to acylated product within 24 hours. The relative concentrations of the reactants in the exemplary example are typical of one preferred embodiment.

In some embodiments, activated charcoal is added in sufficient amount to sequester at least 20%, at least 30%, at least 40%, at least 50%, at least 60%, at least 70%, at least 75%, at least 80%, at least 85%, and at least 90% of thiol byproduct, preferably in sufficient amount to sequester 95% of thiol byproduct, and most preferably in sufficient amount to sequester at least 98% of thiol byproduct. Activated charcoal may also be added in proportion to the amount of solvent; for example, 2-20 grams of activated charcoal may be added per liter of solvent. Preferably, 5-15 grams of activated charcoal are added per liter of solvent. Most preferably, about 10 grams of activated charcoal are added per liter of solvent. Addition of activated charcoal in one embodiment is made prior to the addition of both enzyme and donor molecule. Clarification of a substrate, such as during the workup of a reaction, may sometimes involve the use of activated charcoal. A person of skill in the art will appreciate that the use of activated charcoal in this manner does not provide an improved enzymatic reaction because maximal conversion has already been achieved and the advantage of increased enzymatic rate is no longer achievable.

Precipitating agents can produce compounds with reduced solubility including salts. Various salts can be used including salts containing ions of alkali metals and alkaline earth metals such as calcium, barium, lithium, and magnesium. An exemplary precipitating agent may include, for example, calcium hydroxide. Amine salts can also be used including those formed from primary, secondary, tertiary amines, aromatic amines, quaternary ammonium salts, and polyamines thereof. Sequestering agents, including ion exchange resins and other polymeric species, may also be used to effect removal of product from solution.

In another exemplary embodiment, 25 to 200 g/L, also 30 to 150 g/L, and often 50 to 100 g/L (preferably about 75 g/L) of substrate are added to a reaction medium. In addition, 0.25 to 10 g/L, also 0.3 to 8 g/L and often 0.5 to 6 g/L (preferably 0.75 g/L) of LovD enzyme or variant, and 1.0 to 5, also 1.0 to 2.5 and often 1.05 to 1.7 (preferably 1.1) equivalents of thioester are added. The pH is controlled by, for example, a pH stat, which maintains the pH of the system at about 8.5 to 9.5 and preferably 9.0 by titration with ammonium hydroxide. Ammonium hydroxide also functions as a precipitating agent. In preferred embodiments, no buffer is utilized. A typical solvent system may be water. The reaction is preferably run with stirring at room temperature.

Figure 2:
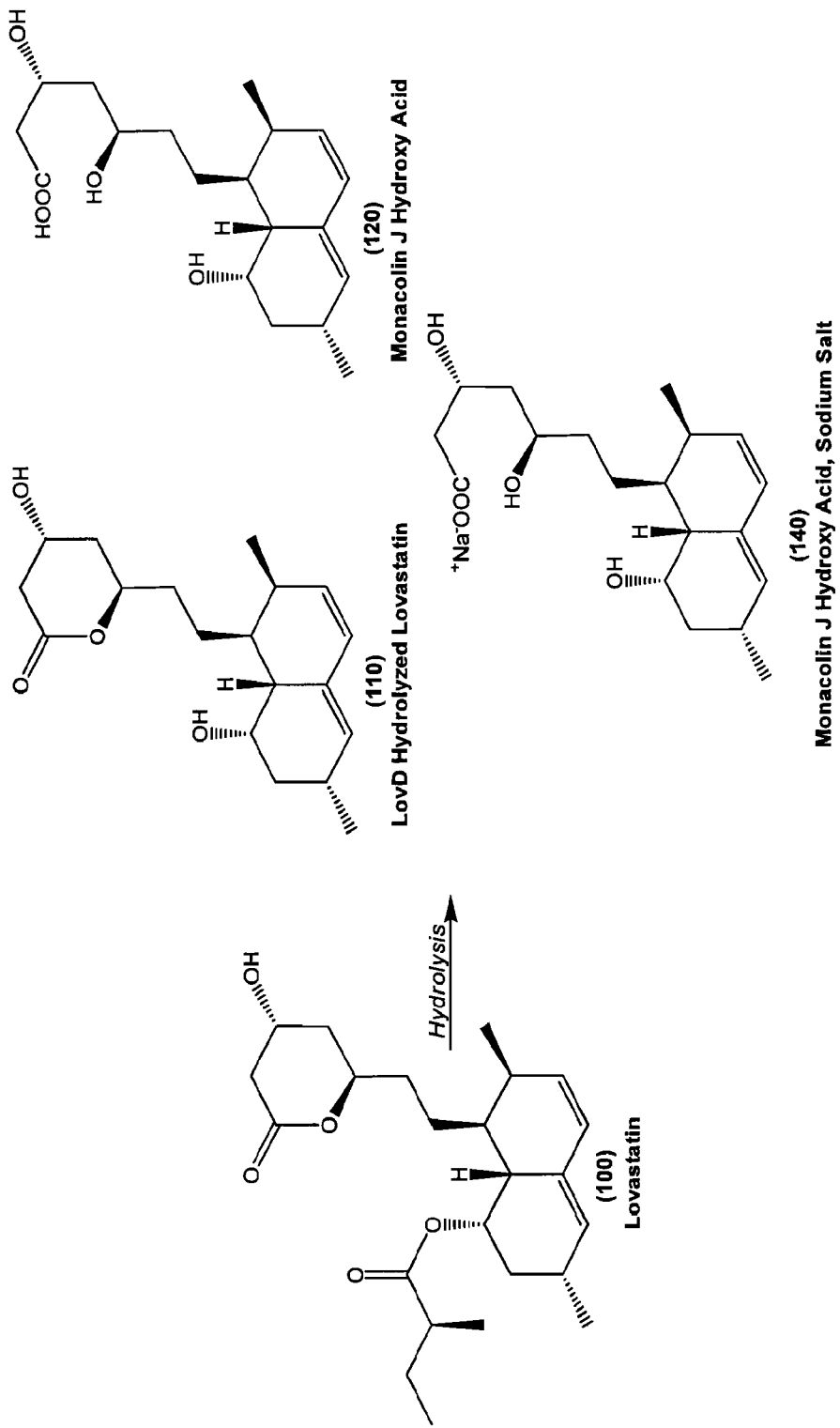
FIG. 2 illustrates the hydrolysis of lovastatin (100), which can be hydrolyzed chemically or enzymatically to produce (a) LovD hydrolyzed lovastatin (110), (b) monacolin J hydroxy acid (120) or (c) monacolin J hydroxy acid, sodium salt (140)

In an exemplary embodiment, simvastatin is produced from lovastatin comprising a first hydrolysis step. Hydrolysis may be effected to provide monacolin J as the free hydroxy acid or the sodium salt of the hydroxy acid. See FIG. 2. Hydrolysis may also be effected in a manner which provides monacolin J as an ammonium salt.

Figure 3:
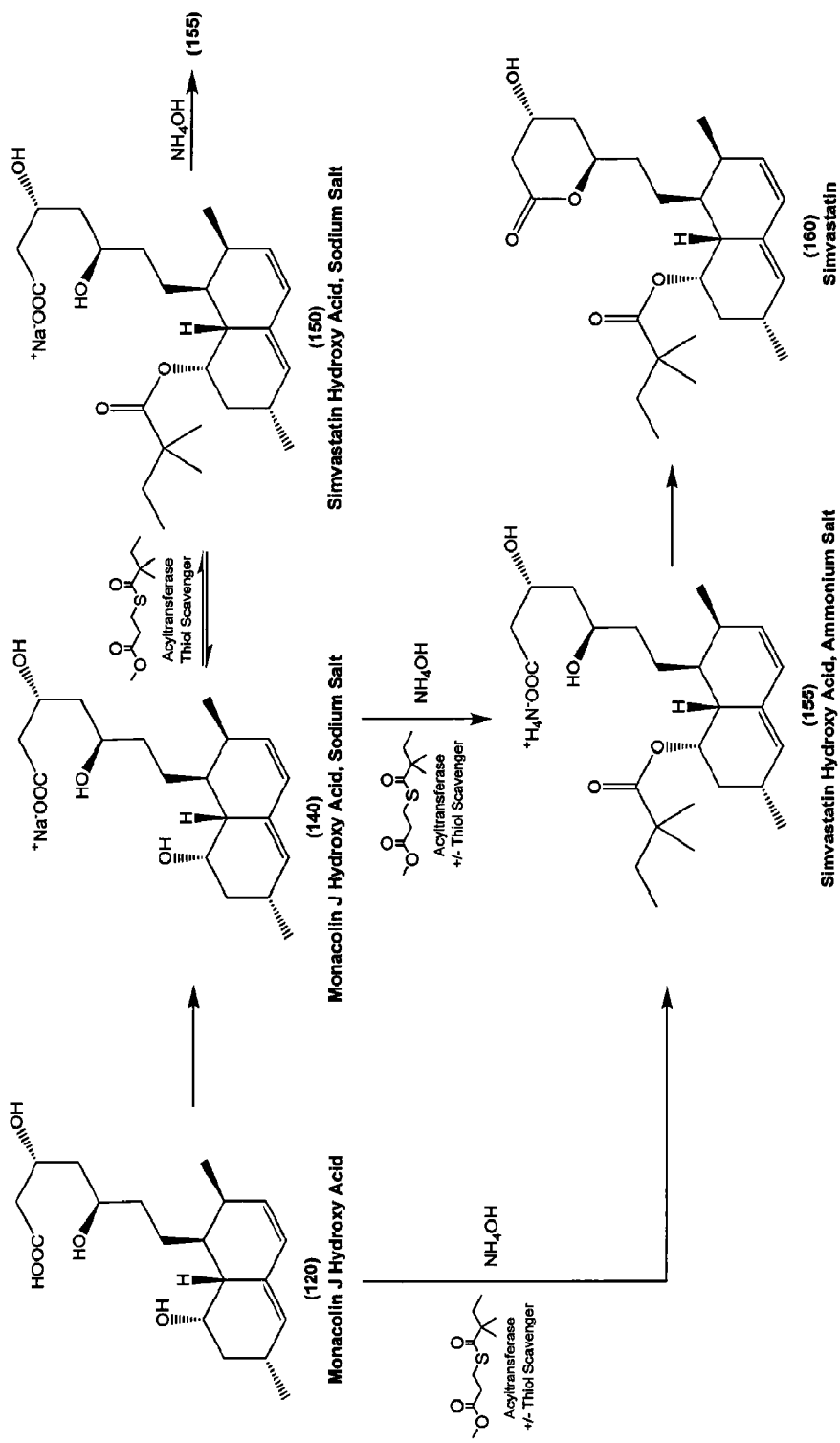
FIG. 3 illustrates various acyltransferase mediated acylations of monacolin J hydroxy acid and its salts.
Figure 4:
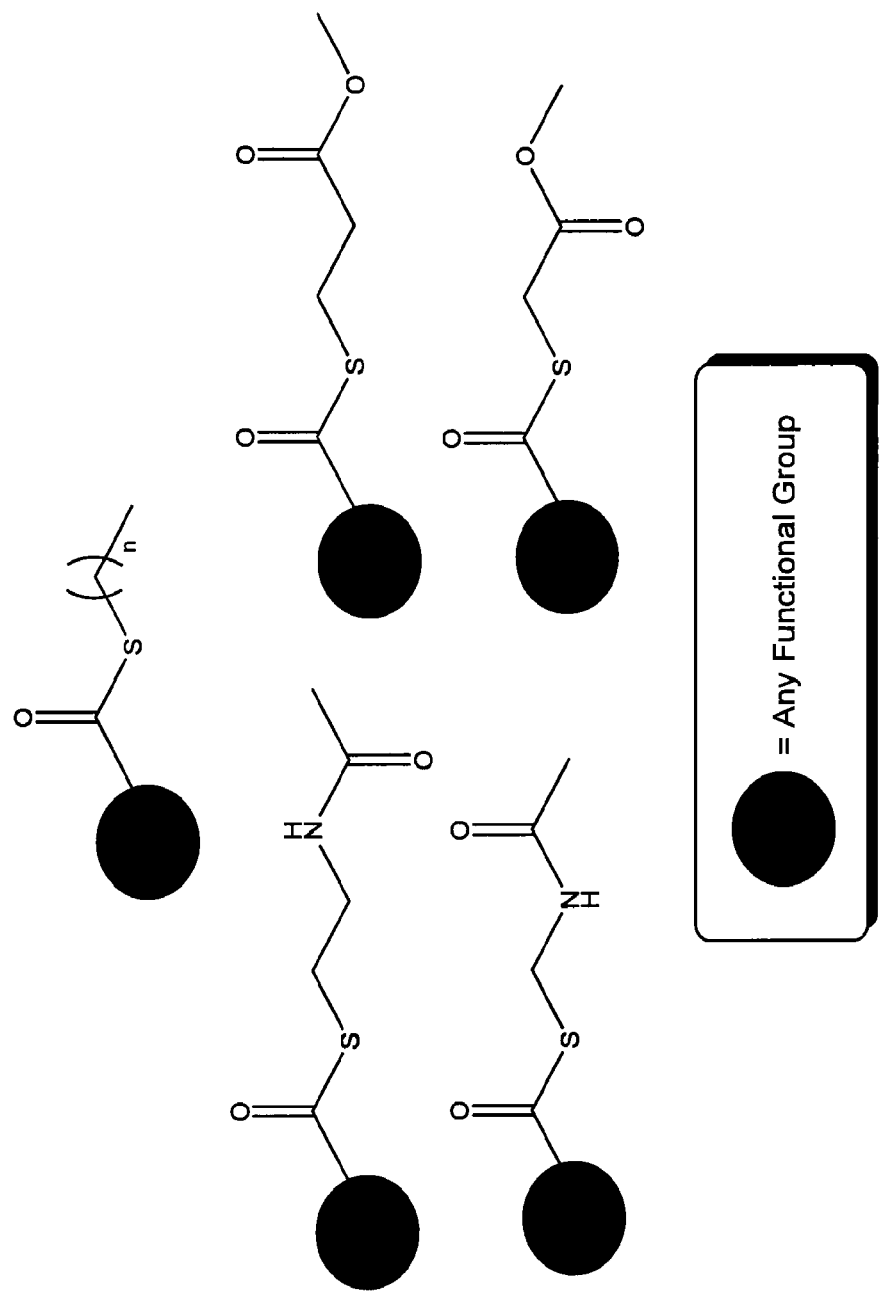
FIG. 4 illustrates some representative thioesters comprising an acyl group.

Monacolin J as the hydroxy acid may be (i) converted to one or more salts such as its corresponding sodium or ammonium salts; and then (ii) acylated to provide a simvastatin precursor compound. When a sodium or other non-ammonium salt of the simvastatin precursor compound is formed, for example, compound 150 of FIG. 3, then the non-ammonium salt may be converted to an ammonium salt (155). Lactonization of the ammonium salt (155) provides simvastatin (160). Alternatively, when an ammonium salt of monacolin J is used, monacolin J ammonium salt may be acylated directly to the ammonium salt simvastatin precursor (155). Some of the various routes to simvastatin are illustrated in FIG. 3.

Figure 6:
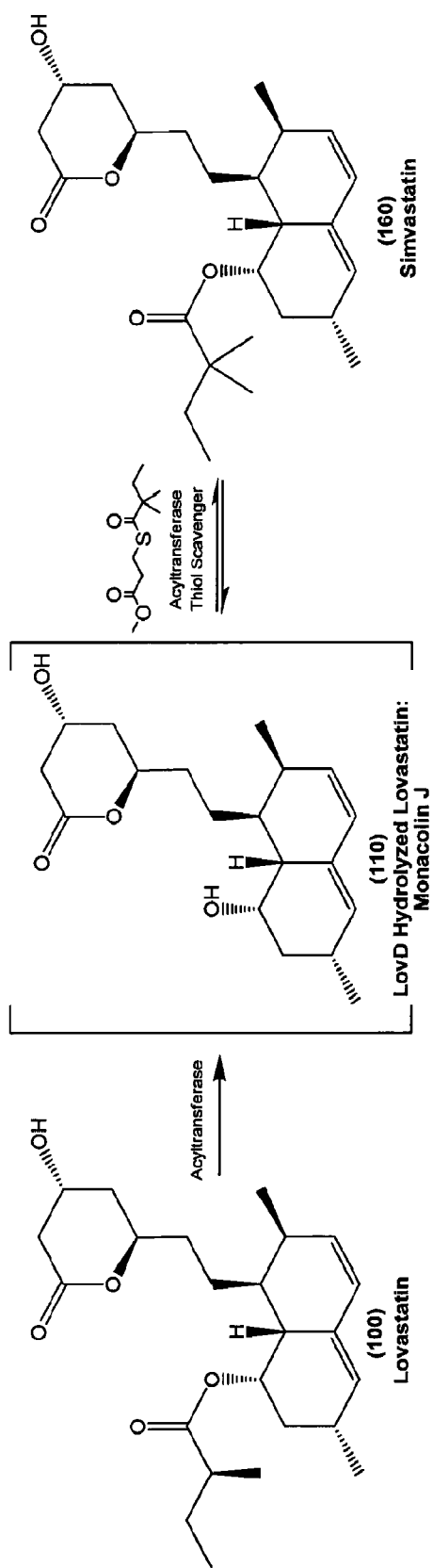
FIG. 6 illustrates the synthesis of simvastatin (160) from lovastatin (100) via a LovD hydrolyzed lovastatin (110).

Acyltransferase may also be used to effect one or more hydrolysis steps in addition to the acylation of lovastatin. For example, LovD acyltransferase may be used to effect hydrolysis of lovastatin into a LovD hydrolyzed lovastatin (monacolin J lactone) and acylation of the free hydroxyl at C8. See FIG. 6.

In practicing the methods of the disclosure, various amounts of substrate, reactant, and reaction conditions may be used to carry out the methods of one or more embodiments. Adjustable parameters include the concentration of substrate in solution, the number of equivalents of the acyl donor relative to the substrate, buffer type and concentration, weight loading, atmospheric conditions, such as partial pressure and gas type, e.g., air, nitrogen, oxygen, argon, etc., the amount of thiol scavenger (if present), the amount of precipitating agent (if present), reaction pH, temperature, and stir-rate, the presence or absence of co-solvent, reaction time, and the manner in which the substrate is isolated or prepared for further reaction.

In one or more embodiments, monacolin J hydroxy acid, sodium salt is reacted at a substrate loading between about 1 to 250 g/L, often 1 g/L to 150 g/L or 50 g/L to 150 g/L. Preferably, monacolin J hydroxy acid, sodium salt is reacted at a substrate loading between 75 g/L and 150 g/L. Most preferably, monacolin J hydroxy acid, sodium salt is reacted using a substrate loading of about 75 g/L. A skilled artisan will appreciate that the substrate loading values may readily be converted into a molarity, wherein molarity is a measure of the concentration of a solute in solution. For example, a 75 g/L loading of the monacolin J hydroxy acid (MJ), sodium salt has an approximate molarity of 0.21 M (75 g/L MJ×(1 mol/360.42 g MJ)). In other embodiments, substrates other than monacolin J hydroxy acid, sodium salt may be acylated according to the methods of the disclosure. Preferably, such acylations will occur with a substrate concentration having a molarity within the ranges given for monacolin J hydroxy acid, sodium salt. For example, a highly preferred reaction condition for acylation of a substrate is a substrate molarity of about 0.21 M.

The reaction can be carried out under a variety of different reaction conditions. Typically the reaction is carried out comprising about 0.2 to 10 g/L, often 0.25 to 5 g/L, variant LovD polypeptide, from about 1 to 250 g/L, often 50 to 150 g/L, monacolin J substrate (or a salt thereof) and from about 1 to 10 equiv, often 1 to 2 equiv, α-dimethylbutyryl thioester co-substrate. The reaction is typically carried out in an aqueous buffer (0 to 300 mM, preferably 50 to 300 mM, more preferably 200 mM) having a pH in the range of pH 7.5 to 10.5, often pH 8.0 to 9.5 or pH 8.5 to 9.5. The identity of the buffer is not critical. Suitable buffers include, but are not limited to, triethanolamine (TEA), potassium phosphate, or a buffer may not be used.

Aqueous co-solvent systems can also be used. Such co-solvents will typically include from about 1 to 10% of a polar organic co-solvent. Suitable polar organic co-solvents include, but are not limited to, MeCN, DMSO, isopropyl alcohol (IPA), dioxane, THF, acetone, and MeOH.

In one or more embodiments, the acyl donor is charged to the reaction vessel in a concentration between about 1.0 or 1.05 and about 4 equivalents relative to substrate. In preferred embodiments, the thioester is present in an amount between 1.1 and 2.0 equivalents relative to substrate. More preferably, the thioester is present in an amount between 1.1 and 1.7 equivalents.

It has been found that in certain acylations of a substrate using LovD acyltransferase, pH may affect reaction progression. Accordingly, in one or more embodiments, the acyltransferase reaction occurs at a pH of greater than 7. Preferably, the pH is greater than 8. More preferably, the pH is between about 8.0 and 10.5 and most preferably, the pH is between about 8.0 and 9.5.

The acylation reaction may be effected at various temperatures, including between 15° C. and 45° C., also between 20° C. and 40° C., and between 20° C. and 35° C. Preferably, the reaction occurs at a temperature between 22° C. and 28° C. Most preferably, the reaction occurs at about 25° C. Preferably, the acylation reaction occurs with stirring. In some instances, a cosolvent may be added to aid in complete solvation of one or more components of the reaction medium or to prevent the formation of intractable slurries. In preferred embodiments, the acylation of monacolin J hydroxy acid, sodium salt or ammonium salt, does not require addition of cosolvent.

In some embodiments, a controlled feed of substrate, such as but not limited to substrate in solution, is added. For example, a syringe pump can be used to deliver a controlled feed of substrate dissolved in a solvent system. In an alternative embodiment, substrate may be added in batches, for example, an initial charge of substrate is followed at some period of time later by a second charge. In yet another embodiment, a single charge may be followed by a controlled feed of substrate.

Reaction time is preferably of sufficient length to allow complete conversion of substrate to target product. In a preferred embodiment using monacolin J hydroxy acid, sodium salt in a preferred amount and using preferred conditions, the reaction is allowed to proceed between 2 and 48 hours before workup. In some preferred embodiments, the course of the reaction is monitored by suitable methods. The reaction is quenched or otherwise "worked-up" when monitoring indicates no appreciable degree of additional conversion of substrate to target product. Isolation may involve extraction. In one preferred embodiment, one or more volumes of methyl tert-butyl ether (MTBE) are used to perform a first extraction before adjustment of the aqueous phase pH and subsequent extraction with ethyl acetate (EtOAc) as described below in the examples. A skilled artisan will appreciate that reaction time and workup conditions for various substrates may be determined using known methods and no more than routine experimentation.

It is contemplated that excess thioester may be recovered from one or more waste streams. For example, in one embodiment, excess or unreacted thioester is extracted into MTBE. The MTBE extract can then undergo one or more aqueous washes, preferably basic aqueous washes, to remove thiol byproduct. The purified thioester may then resubjected to reaction conditions as either a crude recycled material or as a blend with fresh thioester. In some embodiments, the recycled thioester is distilled to increase purity prior to addition to the reaction medium.

The order of addition of materials may vary in one or more embodiments. For example, the following orders of addition may be used: enzyme, scavenger, thioester; scavenger, enzyme, thioester; or scavenger, thioester, enzyme. In embodiments where a scavenger is not utilized, enzyme or thioester may be added first to the reaction medium.

In some embodiments, the process comprises the acylation of a simvastatin precursor using (i) a precipitating agent and/or (ii) a sequestering agent. In an aspect of one or more embodiments, a skilled artisan can assess the solubility of simvastatin salts. For example, a skilled artisan could generate the sodium, potassium, calcium, magnesium, and ammonium salts of simvastatin or a precursor thereof. The skilled artisan could then assess these salts in various solvent systems. The skilled artisan would then compare the solubility of these salts in a given solvent system against the solubility of the corresponding monacolin J salt. Monacolin J salts which are soluble in the given solvent system which produce simvastatin salts which have reduced solubility (or low or no solubility) in the solvent system can then be used in a process for producing simvastatin which utilizes the precipitation of product to favorably shift the equilibrium of the reaction.

The various methods and processes described herein are not limited to the use of any specific LovD acyltransferase enzyme, and can be carried out with any LovD acyltransferase capable of catalyzing the desired acyl transfer. LovD acyltransferases useful in the processes and methods described herein include, but are not limited to, the wild-type LovD acyltransferase obtainable from *A. terreus* (the amino acid sequence of which is provided as SEQ ID NO:2; see also WO 00/037692 and WO 2007/139871), the various mutants of this wild-type LovD acyltransferase described in, for example, Biotechnol Bioeng, 2009 Jan. 1; 102(1):20-8, and the various variants described in U.S. Patent Application No. 61/247,253, filed Sep. 30, 2009, titled "Variant LovD Polypeptides and Their Uses" and U.S. Patent Application No. 12/890,134, filed Sep. 24, 2010, issued as U.S Pat. No. 8,383,382, both of which are collectively referred to as the "Variant Applications."

As disclosed in the Variant Applications, numerous variant LovD acyltransferases have been discovered that have improved properties as compared to the wild-type LovD acyltransferase of SEQ ID NO:2. All of these LovD variants can be advantageously used in the methods and processes described herein. For example, as disclosed in the above applications, such LovD variant acyltransferases include one or more mutations at selected positions that correlate with one or more improved properties, such as increased catalytic activity, increased thermal stability, reduced aggregation and/or increased stability to cell lysis conditions. The variant LovD acyltransferases can include one or more mutations from a single category (for example, one or more mutations that increase catalytic activity), or mutations from two or more different categories. By selecting mutations correlating with specific properties, variant LovD polypeptides suitable for use under specified conditions can be readily obtained.

Positions in the wild-type LovD acyltransferase of sequence of SEQ ID NO:2 at which mutations have been found that correlate with one or more improved properties, such as increased catalytic activity include, but are not limited to, A123, M157, S164, S172, L174, A178, N191, L192, A247, R250, S256, A261, G275, Q297, L361, V370 and N391. Specific, exemplary mutations of the wild-type LovD acyltransferase of SEQ ID NO:2 that correlate with increased catalytic activity include, but are not limited to, A123P, M157V, S164G, S172N, L174F, A178L, N191G, L192I, A247S, R250K, S256T, A261H, G275S, Q297G, L361M, V370I and N391S.

Additional positions at which mutations have been found which correlate with one or more improved properties, such as thermal stability, include, but are not limited to, Q241, A261, Q295 and Q412. Specific, exemplary mutations of the wild-type LovD acyltransferase of SEQ ID NO:2 that correlate with increased thermal stability include, but are not limited to, Q241M, A261H, Q295R and Q412R.

Yet further positions at which mutations have been found that correlate with one or more improved properties, such as reduced aggregation, include but are not limited to, N43, D96 and H404. Specific, exemplary mutations of the wild-type LovD acyltransferase of SEQ ID NO:2 that correlate with reduced aggregation include, but are not limited to, N43R, D96R and H404K.

Still further positions at which mutations were found that correlated with one or more improved properties, such as increased stability include, but are not limited to, C40, C60 and D254. Specific exemplary mutations of the wild-type LovD acyltransferase of SEQ ID NO:2 that correlate with increased stability include, but are not limited to, C40R, C60R and D254E.

Positions were also discovered that could be mutated without detrimental effect, whether or not such mutations conferred the LovD acyltransferase with improved properties. Positions within the wild-type LovD acyltransferase sequence of SEQ ID NO:2 which can be mutated without detrimental effect include, but are not limited to, I4, A9, K26, R28, I35, C40, S41, N43, C60, S109, S142, A184V, N191S, A261, L292, Q297, L335, A377, A383, N391 and H404. Specific, exemplary mutations that can be incorporated at these positions include, but are not limited to, I4N, A9V, K26E, R28K, R28S, I35L, C40A, C40V, C40F, S41R, N43Y, C60F, C60Y, C60N, C60H, S109C, S142N, A184T, A184V, N191S, A261T, A261E, A261V, L292R, Q297E, L335M, A377V, A383V, N391D and H404R.

LovD acyltransferases having sequences that correspond to SEQ ID NO:2 and that include one or more mutations at any of the positions mentioned above are useful in the methods and processes described herein. In a specific embodiment, useful LovD acyltransferases have sequences that correspond to SEQ ID NO:2 and include mutations at positions L174 and A178 (in a specific embodiment L174F and A178L), and optionally from 1 to about 30 additional mutations, which may be selected form the positions and residues discussed above. In another specific embodiment, useful LovD acyltransferases have sequences that correspond to SEQ ID NO:2 and include at least the following mutations: A123P, L174F, A178L, N191(S or G), A247S and L361M, and from zero up to about 26 additional mutations, which may be selected from the various different positions and mutations discussed above.

As disclosed in the Variant Applications, it is believed that the amino acid at position 76 may be involved in catalysis. Mutations at this residue position should be preferably avoided. It is also believed that the amino acids at position 79, 148, 188 and/or 363 may contribute to catalysis. Mutations at these positions are likewise preferably avoided.

In addition to the mutations described above, useful LovD acyltransferases may also include conservative mutations at one or more positions (independently of or in addition to the mutations discussed above). Generally, wild-type and variant LovD acyltransferases including conservative mutations will contain from 1 to 20 such mutations. In additional embodiments, wild-type and variant LovD acyltransferases that are truncated at one or both termini and that retain their catalytic activity may be used in the methods and processes described herein. In some embodiments, such truncated LovD acyltransferases include wild-type or variant LovD acyltransferases in which 1 to 15 amino acids are omitted from the N-terminus and/or from 1 to 6 amino acids are omitted from the C-terminus.

Specific embodiments of variant LovD acyltransferases having improved catalytic activity as compared to the wild-type acyltransferase of SEQ ID NO:2 that are useful in the methods and processes described herein are provided in Table 2, below:

TABLE 2

| Variant No. | Mutations (Relative to SEQ ID NO: 2) | Activity* |
|---|---|---|
| 120 | A123P; L174F; A178L; N191S; A247S; L361M; | + |
| 4 | I35L; A123P; L174F; A178L; N191S; A247S; L361M; | + |
| 6 | A123P; L174F; A178L; N191S; A247S; G275S; L361M; | + |
| 8 | A123P; L174F; A178L; N191S; A247S; R250K; L361M; | + |
| 10 | A123P; L174F; A178L; N191S; A247S; Q297E; L361M; | + |
| 12 | R28K; A123P; L174F; A178L; N191S; A247S; L361M; | + |
| 14 | A123P; L174F; A178L; A184T; N191S; A247S; L361M; | + |
| 16 | A123P; L174F; A178L; N191S; A247S; Q297E; L361M; | + |
| 18 | A123P; L174F; A178L; N191S; L192I; A247S; L361M; | + |
| 20 | A123P; L174F; A178L; N191S; A247S; R250K; L361M; | + |
| 22 | A123P; L174F; A178L; N191S; A247S; A261E; L361M; | + |
| 24 | A123P; L174F; A178L; N191S; A247S; L361M; H404R; | + |
| 26 | K26E; A123P; L174F; A178L; N191S; A247S; L361M; | + |
| 28 | A123P; S172N; L174F; A178L; N191S; A247S; G275S; L361M; | ++ |
| 30 | A123P; M157V; S172N; L174F; A178L; N191S; A247S; G275S; L361M; | ++ |
| 32 | A123P; L174F; A178L; N191G; A247S; G275S; L361M; | + |
| 34 | A123P; L174F; A178L; N191S; A247S; G275S; L335M; L361M; | + |
| 36 | A123P; L174F; A178L; N191S; A247S; G275S; L361M; H404K; | + |
| 38 | A123P; L174F; A178L; A184V; N191S; A247S; G275S; L361M; | + |
| 40 | D96R; A123P; L174F; A178L; N191S; A247S; G275S; L361M; | + |
| 42 | A123P; L174F; A178L; N191G; A247S; G275S; L361M; | + |
| 44 | A123P; L174F; A178L; N191S; A247S; G275S; L335M; L361M; | + |
| 46 | A123P; L174F; A178L; N191S; A247S; G275S; L292R; L361M; | + |
| 48 | A123P; L174F; A178L; N191S; L192I; A247S; R250K; G275S; Q297E; L361M; | ++ |
| 50 | A123P; L174F; A178L; N191S; L192I; A247S; R250K; G275S; L361M; | ++ |
| 52 | K26E; C40R; N43Y; A123P; L174F; A178L; N191S; L192I; A247S; G275S; L361M; | ++ |
| 54 | K26E; C40R; A123P; L174F; A178L; N191S; L192I; A247S; G275S; L361M; | ++ |
| 56 | K26E; A123P; L174F; A178L; N191S; A247S; G275S; L361M; | + |
| 58 | A9V; K26E; A123P; M157V; S172N; L174F; A178L; N191S; L192I; A247S; R250K; G275S; Q297E; L361M; A383V; | +++ |
| 60 | K26E; A123P; M157V; S172N; L174F; A178L; N191S; L192I; A247S; R250K; G275S; L361M; | +++ |
| 62 | A123P; M157V; S172N; L174F; A178L; N191G; A247S; G275S; L335M; L361M; | ++ |

TABLE 2-continued

| Variant No. | Mutations (Relative to SEQ ID NO: 2) | Activity* |
|---|---|---|
| 64 | N43R; D96R; A123P; M157V; S172N; L174F; A178L; N191S; A247S; G275S; L361M; H404K; | ++ |
| 66 | A9V; K26E; A123P; M157V; S172N; L174F; A178L; N191S; L192I; A247S; R250K; S256T; G275S; Q297E; L361M; A383V; | +++ |
| 68 | A9V; K26E; S41R; A123P; M157V; S172N; L174F; A178L; N191S; L192I; A247S; R250K; A261V; G275S; Q297E; L361M; A383V; | +++ |
| 70 | A9V; K26E; R28K; A123P; M157V; S164G; S172N; L174F; A178L; N191G; L192I; Q241M; A247S; R250K; G275S; Q297E; L361M; V370I; A383V; | +++ |
| 72 | A9V; K26E; R28K; C40R; A123P; M157V; S164G; S172N; L174F; A178L; N191G; L192I; Q241M; A247S; R250K; G275S; Q297E; L361M; V370I; A383V; | +++ |
| 74 | A9V; K26E; R28K; C40R; A123P; M157V; S164G; S172N; L174F; A178L; N191G; L192I; Q241M; A247S; R250K; G275S; Q297E; L361M; V370I; A383V; | +++ |
| 76 | A9V; K26E; A123P; M157V; S164G; S172N; L174F; A178L; N191G; L192I; A247S; R250K; G275S; Q297E; L361M; V370I; A377V; A383V; | +++ |
| 78 | A9V; K26E; N43R; A123P; M157V; S164G; S172N; L174F; A178L; N191G; L192I; Q241M; A247S; R250K; G275S; Q297E; L361M; V370I; A383V; H404K; | ++++ |
| 80 | A9V; K26E; N43R; D96R; A123P; M157V; S164G; S172N; L174F; A178L; N191G; L192I; Q241M; A247S; R250K; G275S; Q297E; L361M; V370I; A383V; H404K; | ++++ |
| 82 | A9V; K26E; D96R; A123P; M157V; S164G; S172N; L174F; A178L; N191G; L192I; Q241M; A247S; R250K; G275S; Q297E; L361M; V370I; A383V; | ++++ |
| 84 | A9V; K26E; D96R; A123P; M157V; S172N; L174F; A178L; N191G; L192I; Q241M; A247S; R250K; G275S; Q297E; L361M; V370I; A383V; | +++ |
| 86 | A9V; K26E; N43R; D96R; A123P; M157V; S164G; S172N; L174F; A178L; N191G; L192I; A247S; R250K; G275S; Q297E; L361M; V370I; A383V; H404K; | +++ |
| 88 | A9V; K26E; N43R; D96R; A123P; M157V; S164G; S172N; L174F; A178L; N191G; L192I; Q241M; A247S; R250K; G275S; Q297E; L361M; V370I; A383V; | ++++ |
| 90 | A9V; K26E; R28S; N43R; A123P; M157V; S164G; S172N; L174F; A178L; N191G; L192I; Q241M; A247S; R250K; D254E; G275S; Q297E; L361M; V370I; A383V; H404K; | ++++ |
| 92 | A9V; K26E; N43R; A123P; M157V; S164G; S172N; L174F; A178L; N191G; L192I; Q241M; A247S; R250K; A261V; G275S; Q295R; Q297E; L361M; V370I; A383V; H404K; Q412R; | ++++ |
| 94 | A9V; K26E; N43R; A123P; M157V; S164G; S172N; L174F; A178L; N191G; L192I; Q241M; A247S; R250K; A261V; G275S; Q297E; L361M; V370I; A383V; H404K; | ++++ |
| 96 | A9V; K26E; N43R; A123P; M157V; S164G; S172N; L174F; A178L; N191G; L192I; Q241M; A247S; R250K; A261V; G275S; Q295R; Q297E; L361M; V370I; A383V; N391D; H404K; | ++++ |
| 98 | A9V; K26E; N43R; A123P; M157V; S164G; S172N; L174F; A178L; N191G; L192I; Q241M; A247S; R250K; S256T; A261V; G275S; Q297G; L361M; V370I; A383V; N391S; H404K; | ++++ |
| 100 | A9V; K26E; N43R; A123P; M157V; S164G; S172N; L174F; A178L; N191G; L192I; Q241M; A247S; R250K; S256T; A261V; G275S; Q297G; L361M; V370I; A383V; N391S; H404K; | ++++ |
| 102 | A9V; K26E; N43R; S109C; A123P; M157V; S164G; S172N; L174F; A178L; N191G; L192I; Q241M; A247S; R250K; S256T; A261V; G275S; Q297G; L361M; V370I; A383V; N391S; H404K; | ++++ |
| 104 | A9V; K26E; N43R; A123P; M157V; S164G; S172N; L174F; A178L; N191G; L192I; Q241M; A247S; R250K; S256T; A261H; G275S; Q297G; L361M; V370I; A383V; N391S; H404K; | ++++ |
| 106 | A9V; K26E; N43R; A123P; M157V; S164G; S172N; L174F; A178L; N191G; L192I; Q241M; A247S; R250K; S256T; A261H; G275S; Q295R; Q297G; L361M; V370I; A383V; N391S; H404K; Q412R; | ++++ |
| 108 | I4N; A9V; K26E; R28S; N43R; A123P; M157V; S164G; S172N; L174F; A178L; N191G; L192I; Q241M; A247S; R250K; S256T; A261H; G275S; Q297G; L361M; V370I; A383V; N391S; H404K; | ++++ |
| 110 | I4N; A9V; K26E; R28S; N43R; A123P; M157V; S164G; S172N; L174F; A178L; N191G; L192I; Q241M; A247S; R250K; D254E; S256T; A261H; G275S; Q297G; L361M; V370I; A383V; N391S; H404K; | ++++ |
| 112 | I4N; A9V; K26E; R28S; N43R; S109C; A123P; M157V; S164G; S172N; L174F; A178L; N191G; L192I; Q241M; A247S; R250K; S256T; A261H; G275S; Q295R; Q297G; L361M; V370I; A383V; N391S; H404K; Q412R; | ++++ |
| 114 | I4N; A9V; K26E; R28S; I35L; N43R; D96R; A123P; M157V; S164G; S172N; L174F; A178L; N191G; L192I; Q241M; A247S; R250K; S256T; A261H; G275S; Q297G; L335M; L361M; V370I; A383V; N391S; H404K; | ++++ |
| 116 | I4N; A9V; K26E; R28S; I35L; N43R; D96R; S109C; A123P; M157V; S164G; S172N; L174F; A178L; N191G; L192I; Q241M; A247S; R250K; S256T; A261H; G275S; Q297G; L335M; L361M; V370I; A383V; N391S; H404K; | ++++ |

TABLE 2-continued

| Variant No. | Mutations (Relative to SEQ ID NO: 2) | Activity* |
|---|---|---|
| 118 | I4N; A9V; K26E; R28S; I35L; C40R; N43R; C60R; D96R; S109C; A123P; M157V; S164G; S172N; L174F; A178L; N191G; L192I; Q241M; A247S; R250K; D254E; S256T; A261H; G275S; Q297G; L335M; L361M; V370I; A383V; N391S; H404K; | ++++ |

*Activity relative to the wild-type LovD acyltransferase of SEQ ID NO: 2. A relative activity of "+" exhibited from about 10 to 50-fold greater activity than wild-type; variants with a relative activity of "++" exhibited from about 50 to 100-fold greater activity than wild type; variants with a relative activity of "+++" exhibited from about 100 to 500-fold greater activity than wild type; and variants with a relative activity of "++++" exhibited from about 500 to 2000-fold greater activity than wild type

7. EXAMPLES

The following Examples are illustrative of one or more embodiments and as such are not to be considered as limiting the scope of the claims appended hereto.

Example 1

Preparation of Methyl 3-(2,2-Dimethylbutanoylthio)propionate

A solution of N,N-diisopropylethylamine (19.9 mL, 120 mmol) and methyl 3-mercaptopropanoate (7.21 60 mmol) in isopropyl acetate (i-PrOAc, 100 mL) was cooled to an internal temperature of 2° C. (brine ice bath). To this vigorously stirred solution was added 2,2-dimethylbutanoyl chloride (8.1 g, 60 mmol) dropwise over 10 min. The resulting suspension was then stirred at 25° C. for 2 h. The reaction was monitored by checking the disappearance of methyl 3-mercaptopropanoate using thin-layer chromatography (TLC) on silica plates. Spots were stained with iodine (eluent: 5% EtOAc/heptane; $R_f$ of methyl 3-mercaptopropanoate: 0.20). The reaction was then quenched by addition of saturated ammonium chloride (100 mL) followed by i-PrOAc (100 mL) and the resultant mixture was stirred until all solid dissolved. The phases were separated and the organic phase was washed successively with 1% aqueous hydrochloric acid (100 mL) and then water (2×50 mL). The organic phase was then dried over sodium sulfate, filtered, and concentrated under reduced pressure (45° C. bath, 50 mm Hg) to obtain a crude mixture as a pale yellow liquid. The crude mixture was subjected to column chromatography over silica gel using a heptane to 2% EtOAc:heptane gradient. Fractions comprising the pure product were combined and concentrated to afford 10.5 g (80%) of methyl 3-(2,2-dimethylbutanoylthio)propionate.

Example 2

Preparation of Monacolin J Hydroxy Acid from Lovastatin

To lovastatin (30 g, 0.074 mol) in a 3-neck round bottom flask (RBF) fitted with a condenser was added isopropanol (IPA, 250 mL). KOH pellets (33.2 g, 0.593 mol) and water (3 mL, 0.1 vol) were then added to the stirred suspension. The reaction was stirred at 80° C. (internal temperature) for 7 h. The reaction was then cooled to ~50° C. and IPA was removed under reduced pressure (35° C., 50 mbar) until a final volume of ~100 mL (3.3 vol) was achieved. Water (110 mL, 3.7 vol) was added to the residue and the solution was cooled to ~10° C. in an ice-water bath. 6 M HCl (92 mL, 3.0 vol) was added dropwise to the solution while maintaining the internal temperature between 12-17° C. The pH of the solution was thereby adjusted to a final pH between 3 and 4. The mixture was then stirred in an ice-bath for 2 h. The solid obtained was filtered off and washed with water (60-90 mL, 2-3 vol) and then with heptane (60 mL, 2 vol). The filter cake was dried in a vacuum oven at 25° C. for 24 h to yield a white solid (22.4 g, 90% yield) with >99% purity by HPLC analysis.

Example 3

Enzymatic Preparation of Simvastatin Hydroxy Acid, Sodium Salt from Monacolin J Hydroxy Acid, in the Absence of a Thiol Scavenger The reaction was run in a 250 mL 3-neck RBF using an overhead stirrer fitted with a flat-blade impeller and an internal thermometer. Execution of the following procedure provided 70-80% of simvastatin hydroxy acid, sodium salt in a single crop as a white solid with a chemical purity of at least 96% according to HPLC analysis. To the RBF was charged, sequentially: monacolin J hydroxy acid (10 g), 1M NaOH (32.5 mL) and deionized water (13 mL). The mixture was stirred until all solid was dissolved prior to the addition of buffer (triethanolamine, 400 mM, pH=8.5, 66 mL). The pH of the resultant mixture was then adjusted from 9.5 to 8.5 with 5 M HCl (1.2 mL) prior to the addition of enzyme. A pH of at least 7.5 was maintained during the course of the reaction. Enzyme (~0.6-0.75 g of LovD acyltransferase or an equivalent amount of a variant thereof) was charged to the stirred mixture as a powder. The mixture was stirred until homogenous.

Thioester (methyl 3-(2,2-dimethylbutanoylthio)-propanoate, 11 mL) was added and the resulting biphasic mixture was stirred at 240 rpm at 25° C. (internal temperature). The reaction course was followed periodically by taking samples from the reaction mixture, quenching, and analyzing. Additional enzyme (0.127 g of LovD or an equivalent amount of a variant thereof) was charged to the stirred mixture after 7 h. After analysis indicated maximum conversion (60-70 hours), the pH of the reaction mixture was adjusted to 9.0 from 7.8 using 10 M NaOH solution (1.6 mL) and the reaction mixture was agitated at 345 rpm for 10 minutes.

Workup of the reaction mixture may be accomplished by first extracting the aqueous phase with methyl tert-butyl ether (MTBE). After extraction with MTBE (2 extractions), the aqueous phase was adjusted to a pH of about 5.3 to 5.4 using 0.5 M HCl while maintaining a temperature below 20° C. The aqueous phase is extracted three times with EtOAc. During each extraction, additional HCl was added, as needed, to maintain the pH of the aqueous phase between 5.3 and 5.4. The EtOAc phases from the 3 extractions were combined. The combined ethyl acetate extracts were filtered through a pad of Celite® (1 g) in a standard G4 sintered glass funnel under reduced pressure to clarify the extract. The filter cake was washed with ethyl acetate (10 mL) and the washings were combined with the filtrate. The filtrate was concentrated as needed or additional EtOAc was added to produce an EtOAc solution with a volume of about 160 mL. This EtOAc solution was used for the next step.

The reaction can be monitored by any suitable method. One suitable and exemplary method included monitoring by HPLC analysis. For example, a 5 μL, aliquot of the reaction mixture was taken and dissolved in 1.0 mL of MeCN:water (95:5). The sample was centrifuged to remove precipitated enzyme and the supernatant was analyzed on a Zorbax Eclipse® C18 column (150×4.6 mm, 5 μm) using a mobile phase gradient of water and 0.1% TFA to MeCN and 0.1% TFA. A sample flow rate of 2.0 mL/min with a detection wavelength of 238 nm, a column temperature of 30° C., and an injection volume of 10 μL was used. Percent conversion was calculated by dividing the sum of the area of detectable simvastatin hydroxy acid and simvastatin over the sum of the areas of detectable monacolin J hydroxy acid, monacolin J lactone, simvastatin hydroxy acid and simvastatin. Monacolin J hydroxy acid and simvastatin hydroxy acid both demonstrated a response factor of 1.

Example 4

Preparation of Simvastatin Hydroxy Acid, Ammonium Salt from Simvastatin Hydroxy Acid, Sodium Salt 160 mL of ethyl acetate solution containing simvastatin hydroxy acid, sodium salt—from Example 3—was charged to a 250 mL 3-neck RBF and the reaction mixture was stirred at 250 rpm at 21° C. A 1:1 (v/v) mixture of ammonium hydroxide (5 mL) and MeOH (5 mL) was then added dropwise over 10 mins to the reaction mixture while maintaining the internal temperature at 21-22° C. After complete addition of the ammonium hydroxide and MeOH mixture, the stirrer speed was increased and the mixture was agitated for 1 h at 21° C. and then for 1 h at 0-5° C. The white solid was then filtered through a standard G4 sintered glass funnel under vacuum and the reaction vessel and filter cake were rinsed with cold EtOAc. The white solid was dried in a vacuum oven (2 mm Hg) at 25° C. for 24 h. This provided 10.48 g (78.2%) isolated yield of simvastatin hydroxy acid, ammonium salt as a white solid with a chemical purity of >96% by HPLC analysis.

Example 5

Enzymatic Preparation of Simvastatin Hydroxy Acid, Sodium Salt from Monacolin J Hydroxy Acid, in the Presence of a Thiol Scavenger A 250 mL 3-neck RBF was equipped with an overhead stirrer, a flat-blade impeller and an internal thermometer. The reaction vessel was charged sequentially with the following: monacolin J hydroxy acid (5 g), 1M NaOH (16.3 mL), and deionized water (6.7 mL). The mixture was stirred until all solid was dissolved prior to the addition of buffer (triethanolamine, 400 mM, pH=8.5, 33.3 mL). The pH of the resultant mixture was adjusted from 9.6 to 9.0 with 5 M HCl (0.12 mL) prior to the addition of enzyme. Enzyme (0.10 g of acyltransferase LovD or an equivalent amount of a variant thereof) was charged to the stirred mixture as a powder. The mixture was stirred until homogeneous. Activated charcoal (0.67 g) was subsequently added and the mixture was stirred for another 5 minutes at 240 rpm at 25° C.

Thioester (methyl 3-(2,2-dimethylbutanoylthio)-propanoate, 5.5 mL) was then added to start the enzymatic reaction. The resulting mixture was stirred at 240 rpm at 25° C. (internal temperature). The reaction course was followed periodically by taking samples from the reaction mixture, quenching, and analyzing using HPLC. After analysis indicated maximum conversion (24 h), the reaction mixture was filtered through a pad of Celite (1.5 g) in a standard G4 sintered glass funnel under reduced pressure to remove the charcoal. The 250 mL 3-neck RBF was rinsed with deionized water (5 mL), which was filtered through the same pad of Celite® and then combined with the filtrate. The filter cake was washed with water (5 mL) and the washings were collected and combined with the filtrate. The filtrate was recharged into a new 250 mL 3-neck flask and the pH of the filtrate was adjusted to 9.0 from 8.2 using 10 M NaOH solution (0.55 mL).

Workup of the reaction mixture was accomplished by first extracting the aqueous phase with methyl tert-butyl ether. After extraction with MTBE (2 extractions), the aqueous phase was adjusted to a pH of about 5.3 to 5.4 using 0.5 M HCl while maintaining a temperature below 20° C. The aqueous phase was extracted three times with EtOAc. During each extraction, additional HCl was added, as needed, to maintain the pH of the aqueous phase between 5.3 and 5.4. The EtOAc phases from the 3 extractions were combined. The combined ethyl acetate extracts were filtered through a pad of Celite® (1 g) in a standard G4 sintered glass funnel under reduced pressure to clarify the extract. The filter cake was washed with ethyl acetate (10 mL) and the washings were combined with the filtrate. The filtrate was concentrated as needed or additional EtOAc was added to produce an EtOAc solution with a volume of about 65 mL. This concentrated EtOAc solution was used for the next step, the formation of simvastatin hydroxy acid, ammonium salt, according to the method of example 4.

Example 6

General Method for the Improved Enzymatic Acylation of a Substrate Using a Thioester and a LovD Acyltransferase To a suitable reaction medium was charged a substrate having a free hydroxyl substituent. Solvent and buffer (as needed) were added. Next, while stirring, thioester (1.1-2.0 eq.) and activated charcoal (~10 g/L of solvent) were added. After homogenization by stirring, the acyltransferase enzyme LovD or a variant thereof (0.01 to 0.2 eq.) were added. The reaction was stirred until completion. Workup included filtration, extraction, and/or concentration to produce the final acylated product.

Example 7

Conversion of Monacolin J Hydroxy Acid to Simvastatin Hydroxy Acid Ammonium Salt and Isolation of Simvastatin Hydroxy Acid Ammonium Salt A 250 mL 3-neck round bottom flask (RBF) was equipped with an overhead stirrer, a flat-blade impeller and an internal thermometer. The reaction vessel was charged with monacolin J hydroxy acid (10 g, 29.58 mmol). Deionized water (112.0 mL) and $NH_4OH$ (4.2 mL) were added subsequently. The mixture was stirred until all solid dissolved prior to the pH adjustment (~2 min). The pH of the resultant mixture was adjusted from 9.2 to 9.0 with 5 M HCl (1.5 mL) prior to the addition of enzyme. LovD enzyme (0.10 g) was charged to the stirred mixture as a powder. The mixture was stirred for 5 minutes at 300 rpm at 25° C. to obtain homogeneity. DMB-S-MMP (methyl 3-(2,2-dimethylbutanoylthio)-propanoate, 7.1 mL, 32.54 mmol, 1.1 eq) was added to start the enzymatic reaction. The resulting biphasic mixture was stirred at 300 rpm at 25° C. (internal temperature). The pH of the reaction was controlled at 9.0 by pH stat and titration with 25% $NH_4OH$ solution. Approximately 97% conversion was obtained after 48 h.

Simvastatin hydroxy acid ammonium salt could be isolated from the above reaction as follows. After in-process analysis indicated maximum conversion, the reaction mixture was filtered through a standard G4 sintered glass funnel under reduced pressure. The 250 mL 3-neck RBF was rinsed with chilled deionized water (10 mL) and the slurry was filtered through the same sintered glass funnel. The filter cake was washed twice with chilled deionized water (20 mL) and then washed three times with MTBE (40 mL). The white solid was dried in a vacuum oven (2 mmHg) at 25° C. for 24 h to afford approximately 11.4 to 11.7 g (85 to 87% isolated yield) of simvastatin hydroxy acid ammonium salt as a white solid with a chemical purity of about 97 to 98% (AUC, 238 nm). In one embodiment, the variant having the mutations described in SEQ ID NO:116 provides good results according to the above conditions. Reaction conditions for the above examples, including loading amounts of substrate or enzyme, may need to be optimized for the reactivity profile of other variants.

All publications, patents, patent applications and other documents cited in this application are hereby incorporated by reference in their entireties for all purposes to the same extent as if each individual publication, patent, patent application or other document were individually indicated to be incorporated by reference for all purposes. While various specific embodiments have been illustrated and described, it will be appreciated that various changes can be made without departing from the spirit and scope of the invention(s).

What is claimed is:

1. A method of making a statin compound, comprising contacting a LovD acyltransferase substrate with a LovD acyltransferase, wherein said LovD acvltransferase is a recombinant variant comprising SEQ ID NO: 2 that includes the mutations L174F and A178L and additional 1 to 30 additional mutations in the presence of a thioester donor and an agent selected from a thiol scavenger, a precipitating agent and combinations thereof, under conditions which yield a statin compound.

2. The method of claim 1 in which the LovD acyltransferase substrate is monacolin J.

3. The method of claim 2, in which the monacolin J is a monacolin J hydroxy acid salt.

4. The method of claim 2 in which the monacolin J is monacolin J lactone.

5. The method of claim 1 in which the LovD acyltransferase substrate is lovastatin.

6. The method of claim 5 in which the lovastatin is a lovastatin hydroxy acid salt.

7. The method of claim 5 in which the lovastatin is lovastatin lactone.

8. The method of claim 1, in which the LovD acyltransferase substrate is 6-hydroxy-6-des-methyl-monacolin-J.

9. The method of claim 8, in which the 6-hydroxyl-6-desmethyl-monacolin J is a 6-hydroxy-6-des-methyl monacolin J hydroxy acid salt.

10. The method of claim 8, in which the 6-hydroxy-6-desmethyl monacolin J is 6-hydroxyl-6-des-methyl monacolin J lactone.

11. The method of claim 1 in which the LovD acyltransferase substrate is pravastatin.

12. The method of claim 11 in which the pravastatin is a pravastatin hydroxy acid salt.

13. The method of claim 11 in which the pravastatin is a pravastatin lactone.

14. The method of claim 1, in which the thioester donor is an alpha-dimethylbutyryl thioester.

15. The method of claim 14 in which the alpha-dimethylbutyryl thioester is selected from the group consisting of α-dimethylbutyryl-S-methyl-mercaptopropionate (DMB-S-MMP), dimethylbutyryl-S-ethyl mercaptopropionate (DMB-S-EMP), dimethylbutyryl-S-methyl thioglycolate (DMB-S-MTG), dimethylbutyryl-S-methyl mercaptobutyrate (DMB-S-MMB), S-2-acetamidoethyl 2,2-dimethylbutanethioate, S-acetamidomethyl 2,2-dimethylbutanethioate and methyl 2-(2,2-dimethylbutanoylthio)acetate.

16. The method of claim 15 in which the alpha-dimethylbutyryl thioester is DMB-S-MMP.

17. The method of claim 14, which is carried out in an aqueous medium at a pH in the range of about pH 8 to pH 9.5.

18. The method of claim 14, which is carried out in an aqueous buffer having an initial pH of about pH 9.

19. The method of claim 14, in which the agent is a thiol scavenging agent.

20. The method of claim 19, in which the thiol scavenging agent is activated charcoal.

21. The method of claim 14, in which the agent is a precipitating agent.

22. The method of claim 21, in which the precipitating agent is ammonium hydroxide.

23. The method of claim 14, in which the LovD acyltransferase is one of the LovD variant selected from the group consist of the variants shown Table 2.

24. The method of claim 14, in which the LovD acyltransferase is a LovD variant comprising SEQ ID NO: 2 that includes the mutations L174F and A178L.

25. A method of making simvastatin hydroxy acid ammonium salt comprising contacting monacolin J or lovastatin with a LovD acyltransferase, wherein said LovD acvltransferase is a recombinant variant comprising SEQ ID NO: 2 that includes the mutations L174F and A178L and additional 1 to 30 additional mutations in the presence of an alpha-dimethylbutyryl thioester donor and ammonium hydroxide under conditions which yield simvastatin hydroxy acid ammonium salt.

26. The method of claim 25, which is carried out in aqueous solution at a pH in the range of about pH 8 to pH 9.5.

27. The method of claim 25, which is carried out in an aqueous buffer having an initial pH of about pH 9.

28. The method of claim 25 in which the said LovD variant comprises SEQ ID NO: 2 that includes L174F and A178L.

29. The method of claim 28, further comprising the following mutations A123P; N191S/G; A247S and L361M.

* * * * *

SEQUENCE LISTING

```
<160> NUMBER OF SEQ ID NOS: 20

<210> SEQ ID NO 1
<211> LENGTH: 1242
<212> TYPE: DNA
<213> ORGANISM: Artificial Sequence
<220> FEATURE:
<223> OTHER INFORMATION: Codon optimized Aspergillus terreus lovD

<400> SEQUENCE: 1
atgggttcta tcattgatgc ggctgcggcc gcggacccgg tggttctgat ggaaacggct      60
ttccgtaaag cggttaaaag ccgccagatt ccgggtgctg ttattatggc gcgtgattgt     120
agtggtaacc tgaactacac tcgctgtttc ggcgcacgca ctgtgcgtcg cgacgagtgc     180
aatcaattac caccgctgca ggtggataca ccatgtcgtc tggcaagcgc tactaaatta     240
ctgaccacga ttatggcact gcagtgcatg gaacgcggcc tggtagactt ggatgaaact     300
gttgaccgcc tgctgccgga cctgagcgcg atgccggtgc tggaaggctt tgatgatgcc     360
ggcaacgccc gtctgcgcga acgccgtggt aaaattacgt tacgccatct gctgacacac     420
accagcggtc tgtcgtacgt cttcctgcat ccgctgctgc gcgagtatat ggcccagggt     480
catttgcaga gcgctgagaa gtttggcatt cagtctcgtc tggcgccgcc agctgttaat     540
gatccaggcg cggaatggat ttatggcgct aatctggact gggcaggcaa attagtggaa     600
cgcgcaacgg gcttggacct ggaacagtac ttgcaggaga catttgcgc gccgctgggc     660 atcactgata tgacgttcaa actgcagcag cgtccggata tgctggcacg tcgtgccgac     720
cagacccacc gcaactccgc ggatggtcgt ctgcgctatg atgactctgt gtattttcgc     780
gcggacggtg aagagtgttt cggggggccag ggcgtgttca gcggtccagg cagttacatg     840
aaggttctgc actctctgct gaaacgtgac ggcctgttgc tgcagccaca aaccgtggat     900
ctgatgttcc agccggcgct ggaaccgcgc ttggaagaac aaatgaacca gcatatggac     960
gcgtcgccgc acatcaacta tggcggtcca atgcctatgg tcctgcgtcg cagcttcggc    1020
ctgggtggta tcattgcact ggaggatctg gatggtgaga actggcgtcg taaaggctcg    1080
ctgacgtttg gtggcggtcc aaacattgtt tggcagattg acccgaaagc gggtctgtgt    1140
actttagcct ttttccagct ggaaccgtgg aacgacccgg tgtgtcgtga cctgactcgc    1200
acctttgagc acgcgatcta tgcacagtat caacagggct aa                        1242

<210> SEQ ID NO 2
<211> LENGTH: 413
```

<212> TYPE: PRT
<213> ORGANISM: Artificial Sequence
<220> FEATURE:
<223> OTHER INFORMATION: Codon optimized Aspergillus terreus lovD

<400> SEQUENCE: 2

Met Gly Ser Ile Ile Asp Ala Ala Ala Ala Asp Pro Val Val Leu
1               5                   10                  15

Met Glu Thr Ala Phe Arg Lys Ala Val Lys Ser Arg Gln Ile Pro Gly
            20                  25                  30

Ala Val Ile Met Ala Arg Asp Cys Ser Gly Asn Leu Asn Tyr Thr Arg
            35                  40                  45

Cys Phe Gly Ala Arg Thr Val Arg Arg Asp Glu Cys Asn Gln Leu Pro
    50                  55                  60

Pro Leu Gln Val Asp Thr Pro Cys Arg Leu Ala Ser Ala Thr Lys Leu
65                  70                  75                  80

Leu Thr Thr Ile Met Ala Leu Gln Cys Met Glu Arg Gly Leu Val Asp
                85                  90                  95

Leu Asp Glu Thr Val Asp Arg Leu Leu Pro Asp Leu Ser Ala Met Pro
                100                 105                 110

Val Leu Glu Gly Phe Asp Ala Gly Asn Ala Arg Leu Arg Glu Arg
            115                 120                 125

Arg Gly Lys Ile Thr Leu Arg His Leu Leu Thr His Thr Ser Gly Leu
130                 135                 140

Ser Tyr Val Phe Leu His Pro Leu Leu Arg Glu Tyr Met Ala Gln Gly
145                 150                 155                 160

His Leu Gln Ser Ala Glu Lys Phe Gly Ile Gln Ser Arg Leu Ala Pro
                165                 170                 175

Pro Ala Val Asn Asp Pro Gly Ala Glu Trp Ile Tyr Gly Ala Asn Leu
            180                 185                 190

Asp Trp Ala Gly Lys Leu Val Glu Arg Ala Thr Gly Leu Asp Leu Glu
        195                 200                 205

Gln Tyr Leu Gln Glu Asn Ile Cys Ala Pro Leu Gly Ile Thr Asp Met
210                 215                 220

Thr Phe Lys Leu Gln Gln Arg Pro Asp Met Leu Ala Arg Arg Ala Asp
225                 230                 235                 240

Gln Thr His Arg Asn Ser Ala Asp Gly Arg Leu Arg Tyr Asp Asp Ser
                245                 250                 255

Val Tyr Phe Arg Ala Asp Gly Glu Glu Cys Phe Gly Gly Gln Gly Val
            260                 265                 270

Phe Ser Gly Pro Gly Ser Tyr Met Lys Val Leu His Ser Leu Leu Lys
        275                 280                 285

Arg Asp Gly Leu Leu Leu Gln Pro Gln Thr Val Asp Leu Met Phe Gln
290                 295                 300

Pro Ala Leu Glu Pro Arg Leu Glu Glu Gln Met Asn Gln His Met Asp
305                 310                 315                 320

Ala Ser Pro His Ile Asn Tyr Gly Gly Pro Met Pro Met Val Leu Arg
                325                 330                 335

Arg Ser Phe Gly Leu Gly Gly Ile Ile Ala Leu Glu Asp Leu Asp Gly
            340                 345                 350

Glu Asn Trp Arg Arg Lys Gly Ser Leu Thr Phe Gly Gly Gly Pro Asn
        355                 360                 365

Ile Val Trp Gln Ile Asp Pro Lys Ala Gly Leu Cys Thr Leu Ala Phe
370                 375                 380

```
Phe Gln Leu Glu Pro Trp Asn Asp Pro Val Cys Arg Asp Leu Thr Arg
385                 390                 395                 400

Thr Phe Glu His Ala Ile Tyr Ala Gln Tyr Gln Gln Gly
            405                 410
```

<210> SEQ ID NO 3
<211> LENGTH: 1242
<212> TYPE: DNA
<213> ORGANISM: Artificial Sequence
<220> FEATURE:
<223> OTHER INFORMATION: Variant of lovD

<400> SEQUENCE: 3

```
atgggttcta tcattgatgc ggctgcggcc gcggacccgg tggttctgat ggaaacggct    60
ttccgtaaag cggttaaaag ccgccagatt ccgggtgctg ttattatggc gcgtgattgt   120
agtggtaacc tgaactacac tcgctgtttc ggcgcacgca ctgtgcgtcg cgacgagtgc   180
aatcaattac accgctgcag gtggatacac catgtcgtc tggcaagcgc tactaaatta   240
ctgaccacga ttatggcact gcagtgcatg aacgcggcc tggtagactt ggatgaaact   300
gttgaccgcc tgctgccgga cctgagcgcg atgccggtgc tggaaggctt tgatgatgcc   360
ggcaacgccc gtctgcgcga acgccgtggt aaaattacgt tacgccatct gctgacacac   420
accagcggtc tgtcgtacgt cttcctgcat ccgctgctgc gcagtatat ggcccagggt   480
catttgcaga gcgctgagaa gtttggcatt cagtctcgtc tggcgccgcc agctgttaat   540
gatccaggcg cggaatggat ttatggcgct aatctggact gggcaggcaa attagtggaa   600
cgcgcaacgg gcttggacct ggaacagtac ttgcaggaga acatttgcgc gccgctgggc   660
atcactgata tgacgttcaa actgcagcag cgtccggata tgctggcacg tcgtgccgac   720
cagacccacc gcaactccgc ggatggtcgt ctgcgctatg atgactctgt gtattttcgc   780
gcggacggtg aagagtgttt cgggggccag ggcgtgttca gcggtccagg cagttacatg   840
aaggttctgc actctctgct gaaacgtgac ggcctgttgc tgcagccaca aaccgtggat   900
ctgatgttcc agccggcgct ggaaccgcgc ttggaagaac aaatgaacca gcatatggac   960
gcgtcgccgc acatcaacta tggcggtcca atgcctatgg tcctgcgtcg cagcttcggc  1020
ctgggtggta tcattgcact ggaggatctg gatggtgaga actggcgtcg taaaggctcg  1080
atgacgtttg gtggcggtcc aaacattgtt tggcagattg acccgaaagc gggtctgtgt  1140
actttagcct ttttccagct ggaaccgtgg aacgacccgg tgtgtcgtga cctgactcgc  1200
acctttgagc acgcgatcta tgcacagtat caacagggct aa                     1242
```

<210> SEQ ID NO 4
<211> LENGTH: 413
<212> TYPE: PRT
<213> ORGANISM: Artificial Sequence
<220> FEATURE:
<223> OTHER INFORMATION: Variant of lovD

<400> SEQUENCE: 4

```
Met Gly Ser Ile Ile Asp Ala Ala Ala Ala Asp Pro Val Val Leu
1               5                   10                  15

Met Glu Thr Ala Phe Arg Lys Ala Val Lys Ser Arg Gln Ile Pro Gly
                20                  25                  30

Ala Val Ile Met Ala Arg Asp Cys Ser Gly Asn Leu Asn Tyr Thr Arg
            35                  40                  45

Cys Phe Gly Ala Arg Thr Val Arg Arg Asp Glu Cys Asn Gln Leu Pro
        50                  55                  60
```

Pro Leu Gln Val Asp Thr Pro Cys Arg Leu Ala Ser Ala Thr Lys Leu
65                  70                  75                  80

Leu Thr Thr Ile Met Ala Leu Gln Cys Met Glu Arg Gly Leu Val Asp
                85                  90                  95

Leu Asp Glu Thr Val Asp Arg Leu Leu Pro Asp Leu Ser Ala Met Pro
            100                 105                 110

Val Leu Glu Gly Phe Asp Asp Ala Gly Asn Ala Arg Leu Arg Glu Arg
        115                 120                 125

Arg Gly Lys Ile Thr Leu Arg His Leu Leu Thr His Thr Ser Gly Leu
    130                 135                 140

Ser Tyr Val Phe Leu His Pro Leu Leu Arg Glu Tyr Met Ala Gln Gly
145                 150                 155                 160

His Leu Gln Ser Ala Glu Lys Phe Gly Ile Gln Ser Arg Leu Ala Pro
                165                 170                 175

Pro Ala Val Asn Asp Pro Gly Ala Glu Trp Ile Tyr Gly Ala Asn Leu
            180                 185                 190

Asp Trp Ala Gly Lys Leu Val Glu Arg Ala Thr Gly Leu Asp Leu Glu
        195                 200                 205

Gln Tyr Leu Gln Glu Asn Ile Cys Ala Pro Leu Gly Ile Thr Asp Met
210                 215                 220

Thr Phe Lys Leu Gln Gln Arg Pro Asp Met Leu Ala Arg Arg Ala Asp
225                 230                 235                 240

Gln Thr His Arg Asn Ser Ala Asp Gly Arg Leu Arg Tyr Asp Asp Ser
                245                 250                 255

Val Tyr Phe Arg Ala Asp Gly Glu Glu Cys Phe Gly Gln Gly Val
            260                 265                 270

Phe Ser Gly Pro Gly Ser Tyr Met Lys Val Leu His Ser Leu Leu Lys
        275                 280                 285

Arg Asp Gly Leu Leu Leu Gln Pro Gln Thr Val Asp Leu Met Phe Gln
290                 295                 300

Pro Ala Leu Glu Pro Arg Leu Glu Glu Gln Met Asn Gln His Met Asp
305                 310                 315                 320

Ala Ser Pro His Ile Asn Tyr Gly Gly Pro Met Pro Met Val Leu Arg
                325                 330                 335

Arg Ser Phe Gly Leu Gly Gly Ile Ile Ala Leu Glu Asp Leu Asp Gly
            340                 345                 350

Glu Asn Trp Arg Arg Lys Gly Ser Met Thr Phe Gly Gly Pro Asn
        355                 360                 365

Ile Val Trp Gln Ile Asp Pro Lys Ala Gly Leu Cys Thr Leu Ala Phe
    370                 375                 380

Phe Gln Leu Glu Pro Trp Asn Asp Pro Val Cys Arg Asp Leu Thr Arg
385                 390                 395                 400

Thr Phe Glu His Ala Ile Tyr Ala Gln Tyr Gln Gln Gly
                405                 410

<210> SEQ ID NO 5
<211> LENGTH: 1242
<212> TYPE: DNA
<213> ORGANISM: Artificial Sequence
<220> FEATURE:
<223> OTHER INFORMATION: Variant of lovD

<400> SEQUENCE: 5
atgggttcta tcattgatgc ggctgcggcc gcggacccgg tggttctgat ggaaacggct     60

-continued

```
ttccgtaaag cggttaaaag ccgccagatt ccgggtgctg ttattatggc gcgtgattgt      120
agtggtaacc tgaactacac tcgctgtttc ggcgcacgca ctgtgcgtcg cgacgagtgc      180
aatcaattac caccgctgca ggtggataca ccatgtcgtc tggcaagcgc tactaaatta      240
ctgaccacga ttatggcact gcagtgcatg aacgcggcc tggtagactt ggatgaaact       300
gttgaccgcc tgctgccgga cctgagcgcg atgccggtgc tggaaggctt tgatgatgcc     360
ggcaacccgc gtctgcgcga acgcgtggt aaaattacgt tacgccatct gctgacacac      420
accagcggtc tgtcgtacgt cttcctgcat ccgctgctgc gcgagtatat ggcccagggt      480
catttgcaga gcgctgagaa gtttggcatt cagtctcgtt ttgcgccgcc attagttaat     540
gatccaggcg cggaatggat ttatggcgct tctctggact gggcaggcaa attagtggaa    600
cgcgcaacgg gcttgaccct ggaacagtac ttgcaggaga acatttgcgc gccgctgggc    660
atcactgata tgacgttcaa actgcagcag cgtccggata tgctggcacg tcgtgccgac    720
cagacccacc gcaactccag cgatggtcgt ctgcgctatg atgactctgt gtattttcgc     780
gcggacggtg aagagtgttt cggggggccag ggcgtgttca gcggtccagg cagttacatg    840
aaggttctgc actctctgct gaaacgtgac ggcctgttgc tgcagccaca aaccgtggat    900
ctgatgttcc agccggcgct ggaaccgcgc ttggaagaac aaatgaacca gcatatggac    960
gcgtcgccgc acatcaacta tggcggtcca atgcctatgg tcctgcgtcg cagcttcggc  1020
ctgggtggta tcattgcact ggaggatctg gatggtgaga actggcgtcg taaaggctcg  1080
atgacgtttg gtggcggtcc aaacattgtt tggcagattg acccgaaagc gggtctgtgt  1140
actttagcct ttttccagct ggaaccgtgg aacgacccgg tgtgtcgtga cctgactcgc  1200
acctttgagc acgcgatcta tgcacagtat caacagggct aa                     1242
```

<210> SEQ ID NO 6
<211> LENGTH: 413
<212> TYPE: PRT
<213> ORGANISM: Artificial Sequence
<220> FEATURE:
<223> OTHER INFORMATION: Variant of lovD

<400> SEQUENCE: 6

```
Met Gly Ser Ile Ile Asp Ala Ala Ala Ala Asp Pro Val Val Leu
1               5                   10                  15

Met Glu Thr Ala Phe Arg Lys Ala Val Lys Ser Arg Gln Ile Pro Gly
                20                  25                  30

Ala Val Ile Met Ala Arg Asp Cys Ser Gly Asn Leu Asn Tyr Thr Arg
            35                  40                  45

Cys Phe Gly Ala Arg Thr Val Arg Arg Asp Glu Cys Asn Gln Leu Pro
        50                  55                  60

Pro Leu Gln Val Asp Thr Pro Cys Arg Leu Ala Ser Ala Thr Lys Leu
65                  70                  75                  80

Leu Thr Thr Ile Met Ala Leu Gln Cys Met Glu Arg Gly Leu Val Asp
                85                  90                  95

Leu Asp Glu Thr Val Asp Arg Leu Leu Pro Asp Leu Ser Ala Met Pro
                100                 105                 110

Val Leu Glu Gly Phe Asp Asp Ala Gly Asn Pro Arg Leu Arg Glu Arg
            115                 120                 125

Arg Gly Lys Ile Thr Leu Arg His Leu Leu Thr His Thr Ser Gly Leu
        130                 135                 140

Ser Tyr Val Phe Leu His Pro Leu Leu Arg Glu Tyr Met Ala Gln Gly
145                 150                 155                 160
```

His Leu Gln Ser Ala Glu Lys Phe Gly Ile Gln Ser Arg Phe Ala Pro
              165                 170                 175

Pro Leu Val Asn Asp Pro Gly Ala Glu Trp Ile Tyr Gly Ala Ser Leu
         180                 185                 190

Asp Trp Ala Gly Lys Leu Val Glu Arg Ala Thr Gly Leu Asp Leu Glu
     195                 200                 205

Gln Tyr Leu Gln Glu Asn Ile Cys Ala Pro Leu Gly Ile Thr Asp Met
 210                 215                 220

Thr Phe Lys Leu Gln Gln Arg Pro Asp Met Leu Ala Arg Arg Ala Asp
225                 230                 235                 240

Gln Thr His Arg Asn Ser Ser Asp Gly Arg Leu Arg Tyr Asp Asp Ser
             245                 250                 255

Val Tyr Phe Arg Ala Asp Gly Glu Glu Cys Phe Gly Gln Gly Val
         260                 265                 270

Phe Ser Gly Pro Gly Ser Tyr Met Lys Val Leu His Ser Leu Leu Lys
     275                 280                 285

Arg Asp Gly Leu Leu Leu Gln Pro Gln Thr Val Asp Leu Met Phe Gln
 290                 295                 300

Pro Ala Leu Glu Pro Arg Leu Glu Glu Gln Met Asn Gln His Met Asp
305                 310                 315                 320

Ala Ser Pro His Ile Asn Tyr Gly Gly Pro Met Pro Met Val Leu Arg
             325                 330                 335

Arg Ser Phe Gly Leu Gly Gly Ile Ile Ala Leu Glu Asp Leu Asp Gly
         340                 345                 350

Glu Asn Trp Arg Arg Lys Gly Ser Met Thr Phe Gly Gly Pro Asn
     355                 360                 365

Ile Val Trp Gln Ile Asp Pro Lys Ala Gly Leu Cys Thr Leu Ala Phe
 370                 375                 380

Phe Gln Leu Glu Pro Trp Asn Asp Pro Val Cys Arg Asp Leu Thr Arg
385                 390                 395                 400

Thr Phe Glu His Ala Ile Tyr Ala Gln Tyr Gln Gln Gly
             405                 410

<210> SEQ ID NO 7
<211> LENGTH: 1242
<212> TYPE: DNA
<213> ORGANISM: Artificial Sequence
<220> FEATURE:
<223> OTHER INFORMATION: Variant of lovD

<400> SEQUENCE: 7
atgggttcta tcattgatgc ggctgcggcc gcggacccgg tggttctgat ggaaacggct      60
ttccgtaaag cggttaaaag ccgccagatt ccgggtgctg ttattatggc gcgtgattgt     120
agtggtaacc tgaactacac tcgctgtttc ggcgcacgca ctgtgcgtcg cgacgagtgc     180
aatcaattac accgctgcag gtggatacac ccatgtcgtc tggcaagcgc tactaaatta     240
ctgaccacga ttatggcact gcagtgcatg aacgcggcc tggtagactt ggatgaaact      300
gttgaccgcc tgctgccgga cctgagcgcg atgccggtgc tggaaggctt tgatgatgcc     360
ggcaacccgc gtctgcgcga acgccgtggt aaaattacgt tacgccatct gctgacacac     420
accagcggtc tgtcgtacgt cttcctgcat ccgctgctgc gcagtatat ggcccagggt      480 catttgcaga gcgctgagaa gtttggcatt cagtctcgtt ttgcgccgcc attagttaat     540
gatccaggcg cggaatggat ttatggcgct tctctggact gggcaggcaa attagtggaa     600

```
cgcgcaacgg gcttggacct ggaacagtac ttgcaggaga catttgcgc gccgctgggc      660 atcactgata tgacgttcaa actgcagcag cgtccggata tgctggcacg tcgtgccgac      720
cagacccacc gcaactccag cgatggtcgt ctgcgctatg atgactctgt gtattttcgc      780
gcggacggtg aagagtgttt cggggggccag ggcgtgttca gcagtccagg cagttacatg      840
aaggttctgc actctctgct gaaacgtgac ggcctgttgc tgcagccaca aaccgtggat      900
ctgatgttcc agccggcgct ggaaccgcgc ttggaagaac aaatgaacca gcatatggac      960
gcgtcgccgc acatcaacta tggcggtcca atgcctatgg tcctgcgtcg cagcttcggc     1020
ctgggtggta tcattgcact ggaggatctg gatggtgaga actggcgtcg taaaggctcg     1080
atgacgtttg gtggcggtcc aaacattgtt tggcagattg acccgaaagc gggtctgtgt     1140
actttagcct ttttccagct ggaaccgtgg aacgacccgg tgtgtcgtga cctgactcgc     1200
acctttgagc acgcgatcta tgcacagtat caacagggct aa                         1242
```

<210> SEQ ID NO 8
<211> LENGTH: 413
<212> TYPE: PRT
<213> ORGANISM: Artificial Sequence
<220> FEATURE:
<223> OTHER INFORMATION: Variant of lovD

<400> SEQUENCE: 8

```
Met Gly Ser Ile Ile Asp Ala Ala Ala Ala Asp Pro Val Val Leu
1               5                  10                  15

Met Glu Thr Ala Phe Arg Lys Ala Val Lys Ser Arg Gln Ile Pro Gly
            20                  25                  30

Ala Val Ile Met Ala Arg Asp Cys Ser Gly Asn Leu Asn Tyr Thr Arg
        35                  40                  45

Cys Phe Gly Ala Arg Thr Val Arg Arg Asp Glu Cys Asn Gln Leu Pro
    50                  55                  60

Pro Leu Gln Val Asp Thr Pro Cys Arg Leu Ala Ser Ala Thr Lys Leu
65                  70                  75                  80

Leu Thr Thr Ile Met Ala Leu Gln Cys Met Glu Arg Gly Leu Val Asp
                85                  90                  95

Leu Asp Glu Thr Val Asp Arg Leu Leu Pro Asp Leu Ser Ala Met Pro
            100                 105                 110

Val Leu Glu Gly Phe Asp Asp Ala Gly Asn Pro Arg Leu Arg Glu Arg
        115                 120                 125

Arg Gly Lys Ile Thr Leu Arg His Leu Leu Thr His Thr Ser Gly Leu
    130                 135                 140

Ser Tyr Val Phe Leu His Pro Leu Leu Arg Glu Tyr Met Ala Gln Gly
145                 150                 155                 160

His Leu Gln Ser Ala Glu Lys Phe Gly Ile Gln Ser Arg Phe Ala Pro
                165                 170                 175

Pro Leu Val Asn Asp Pro Gly Ala Glu Trp Ile Tyr Gly Ala Ser Leu
            180                 185                 190

Asp Trp Ala Gly Lys Leu Val Glu Arg Ala Thr Gly Leu Asp Leu Glu
        195                 200                 205

Gln Tyr Leu Gln Glu Asn Ile Cys Ala Pro Leu Gly Ile Thr Asp Met
    210                 215                 220

Thr Phe Lys Leu Gln Gln Arg Pro Asp Met Leu Ala Arg Arg Ala Asp
225                 230                 235                 240

Gln Thr His Arg Asn Ser Ser Asp Gly Arg Leu Arg Tyr Asp Asp Ser
                245                 250                 255
```

Val Tyr Phe Arg Ala Asp Gly Glu Glu Cys Phe Gly Gly Gln Gly Val
                260                 265                 270

Phe Ser Ser Pro Gly Ser Tyr Met Lys Val Leu His Ser Leu Leu Lys
            275                 280                 285

Arg Asp Gly Leu Leu Leu Gln Pro Gln Thr Val Asp Leu Met Phe Gln
        290                 295                 300

Pro Ala Leu Glu Pro Arg Leu Glu Glu Gln Met Asn Gln His Met Asp
305                 310                 315                 320

Ala Ser Pro His Ile Asn Tyr Gly Gly Pro Met Pro Met Val Leu Arg
                325                 330                 335

Arg Ser Phe Gly Leu Gly Gly Ile Ile Ala Leu Glu Asp Leu Asp Gly
            340                 345                 350

Glu Asn Trp Arg Arg Lys Gly Ser Met Thr Phe Gly Gly Gly Pro Asn
        355                 360                 365

Ile Val Trp Gln Ile Asp Pro Lys Ala Gly Leu Cys Thr Leu Ala Phe
370                 375                 380

Phe Gln Leu Glu Pro Trp Asn Asp Pro Val Cys Arg Asp Leu Thr Arg
385                 390                 395                 400

Thr Phe Glu His Ala Ile Tyr Ala Gln Tyr Gln Gln Gly
                405                 410

<210> SEQ ID NO 9
<211> LENGTH: 1242
<212> TYPE: DNA
<213> ORGANISM: Artificial Sequence
<220> FEATURE:
<223> OTHER INFORMATION: Variant of lovD

<400> SEQUENCE: 9
atgggttcta tcattgatgc ggctgcggcc gcggacccgg tggttctgat ggaaacggct      60
ttccgtaaag cggttaaaag ccgccagatt ccgggtgctg ttattatggc ggtgattgt     120
agtggtaacc tgaactacac tcgctgtttc ggcgcacgca ctgtgcgtcg cgacgagtgc     180
aatcaattac accgctgcag ggtggataca ccatgtcgtc tggcaagcgc tactaaatta     240
ctgaccacga ttatggcact gcagtgcatg aacgcggcc tggtagactt ggatgaaact     300
gttgaccgcc tgctgccgga cctgagcgcg atgccggtgc tggaaggctt gatgatgcc     360
ggcaacccgc gtctgcgcga acgccgtggt aaaattacgt tacgccatct gctgacacac     420
accagcggtc tgtcgtacgt cttcctgcat ccgctgctgc gcgagtatgt tgcccagggt     480
catttgcaga gcgctgagaa gtttggcatt cagaatcgtt ttgcgccgcc attagttaat     540
gatccaggcg cggaatggat ttatggcgct tctctggact gggcaggcaa attagtggaa     600
cgcgcaacgg gcttggacct ggaacagtac ttgcaggaga cattttgcgc gccgctgggc     660
atcactgata tgacgttcaa actgcagcag cgtccggata tgctggcacg tcgtgccgac     720
cagacccacc gcaactccag cgatggtcgt ctgcgctatg atgactctgt gtattttcgc     780
gcggacggtg aagagtgttt cgggggccag ggcgtgttca gcagtccagg cagttacatg     840
aaggttctgc actctctgct gaaacgtgac ggcctgttgc tgcagccaca aaccgtggat     900
ctgatgttcc agccggcgct ggaaccgcgc ttggaagaac aaatgaacca gcatatggac     960
gcgtcgccgc acatcaacta tggcggtcca atgcctatgg tcctgcgtcg cagcttcggc    1020
ctgggtggta tcattgcact ggaggatctg gatggtgaga ctggcgtcg taaaggctcg    1080
atgacgtttg gtggcggtcc aaacattgtt tggcagattg acccgaaagc gggtctgtgt    1140

```
actttagcct tttccagct ggaaccgtgg aacgacccgg tgtgtcgtga cctgactcgc   1200
acctttgagc acgcgatcta tgcacagtat caacagggct aa                    1242
```

<210> SEQ ID NO 10
<211> LENGTH: 413
<212> TYPE: PRT
<213> ORGANISM: Artificial Sequence
<220> FEATURE:
<223> OTHER INFORMATION: Variant of lovD

<400> SEQUENCE: 10

```
Met Gly Ser Ile Ile Asp Ala Ala Ala Ala Asp Pro Val Val Leu
1               5                   10                  15

Met Glu Thr Ala Phe Arg Lys Ala Val Lys Ser Arg Gln Ile Pro Gly
            20                  25                  30

Ala Val Ile Met Ala Arg Asp Cys Ser Gly Asn Leu Asn Tyr Thr Arg
        35                  40                  45

Cys Phe Gly Ala Arg Thr Val Arg Arg Asp Glu Cys Asn Gln Leu Pro
    50                  55                  60

Pro Leu Gln Val Asp Thr Pro Cys Arg Leu Ala Ser Ala Thr Lys Leu
65                  70                  75                  80

Leu Thr Thr Ile Met Ala Leu Gln Cys Met Glu Arg Gly Leu Val Asp
                85                  90                  95

Leu Asp Glu Thr Val Asp Arg Leu Leu Pro Asp Leu Ser Ala Met Pro
            100                 105                 110

Val Leu Glu Gly Phe Asp Asp Ala Gly Asn Pro Arg Leu Arg Glu Arg
        115                 120                 125

Arg Gly Lys Ile Thr Leu Arg His Leu Leu Thr His Thr Ser Gly Leu
    130                 135                 140

Ser Tyr Val Phe Leu His Pro Leu Leu Arg Glu Tyr Val Ala Gln Gly
145                 150                 155                 160

His Leu Gln Ser Ala Glu Lys Phe Gly Ile Gln Asn Arg Phe Ala Pro
                165                 170                 175

Pro Leu Val Asn Asp Pro Gly Ala Glu Trp Ile Tyr Gly Ala Ser Leu
            180                 185                 190

Asp Trp Ala Gly Lys Leu Val Glu Arg Ala Thr Gly Leu Asp Leu Glu
        195                 200                 205

Gln Tyr Leu Gln Glu Asn Ile Cys Ala Pro Leu Gly Ile Thr Asp Met
    210                 215                 220

Thr Phe Lys Leu Gln Gln Arg Pro Asp Met Leu Ala Arg Arg Ala Asp
225                 230                 235                 240

Gln Thr His Arg Asn Ser Ser Asp Gly Arg Leu Arg Tyr Asp Asp Ser
                245                 250                 255

Val Tyr Phe Arg Ala Asp Gly Glu Glu Cys Phe Gly Gly Gln Gly Val
            260                 265                 270

Phe Ser Ser Pro Gly Ser Tyr Met Lys Val Leu His Ser Leu Leu Lys
        275                 280                 285

Arg Asp Gly Leu Leu Leu Gln Pro Gln Thr Val Asp Leu Met Phe Gln
    290                 295                 300

Pro Ala Leu Glu Pro Arg Leu Glu Glu Gln Met Asn Gln His Met Asp
305                 310                 315                 320

Ala Ser Pro His Ile Asn Tyr Gly Gly Pro Met Pro Met Val Leu Arg
                325                 330                 335

Arg Ser Phe Gly Leu Gly Gly Ile Ile Ala Leu Glu Asp Leu Asp Gly
            340                 345                 350
```

Glu Asn Trp Arg Arg Lys Gly Ser Met Thr Phe Gly Gly Gly Pro Asn
        355                 360                 365

Ile Val Trp Gln Ile Asp Pro Lys Ala Gly Leu Cys Thr Leu Ala Phe
    370                 375                 380

Phe Gln Leu Glu Pro Trp Asn Asp Pro Val Cys Arg Asp Leu Thr Arg
385                 390                 395                 400

Thr Phe Glu His Ala Ile Tyr Ala Gln Tyr Gln Gln Gly
                405                 410

<210> SEQ ID NO 11
<211> LENGTH: 1242
<212> TYPE: DNA
<213> ORGANISM: Artificial Sequence
<220> FEATURE:
<223> OTHER INFORMATION: Variant of lovD

<400> SEQUENCE: 11

```
atgggttcta tcattgatgc ggctgtggcc gcggacccgg tggttctgat ggaaacggct      60
ttccgtaaag cggttgaaag ccgccagatt ccgggtgctg ttattatggc cgtgattgt     120
agtggtaacc tgaactacac tcgctgtttc ggcgcacgca ctgtgcgtcg cgacgagtgc    180
aatcaattac accgctgca ggtggataca ccatgtcgtc tggcaagcgc tactaaatta     240
ctgaccacga ttatggcact gcagtgcatg aacgcggcc tggtagactt ggatgaaact     300
gttgaccgcc tgctgccgga cctgagcgcg atgccggtgc tggaaggctt tgatgatgcc    360
ggcaacccgc gtctgcgcga acgccgtggt aaaattacgt tacgccatct gctgacacac    420
accagcggtc tgtcgtacgt cttcctgcat ccgctgctgc gcgagtatgt tgcccagggt    480
catttgcaga gcgctgagaa gtttggcatt cagaatcgtt ttgcgccgcc attagttaat    540
gatccaggcg cggaatggat ttatggcgct tctatcgact gggcaggcaa attagtggaa    600
cgcgcaacgg gcttggacct ggaacagtac ttgcaggaga catttgcgc gccgctgggc    660
atcactgata tgacgttcaa actgcagcag cgtccggata tgctggcacg tcgtgccgac    720
cagacccacc gcaactccag cgatggtaaa ctgcgctatg atgactctgt gtattttcgc    780
gcggacggtg aagagtgttt cggggggccag ggcgtgttca gcagtccagg cagttacatg    840
aaggttctgc actctctgct gaaacgtgac ggcctgttgc tgcagccaga accgtggat     900
ctgatgttcc agccggcgct ggaaccgcgc ttggaagaac aaatgaacca gcatatggac    960
gcgtcgccgc acatcaacta tggcggtcca atgcctatgg tcctgcgtcg cagcttcggc   1020
ctgggtggta tcattgcact ggaggatctg gatggtgaga ctggcgtcg taaaggctcg   1080
atgacgtttg gtggcggtcc aaacattgtt tggcagattg acccgaaagc gggtctgtgt   1140
actttagtct ttttccagct ggaaccgtgg aacgacccgg tgtgtcgtga cctgactcgc   1200
acctttgagc acgcgatcta tgcacagtat caacagggct aa                      1242
```

<210> SEQ ID NO 12
<211> LENGTH: 413
<212> TYPE: PRT
<213> ORGANISM: Artificial Sequence
<220> FEATURE:
<223> OTHER INFORMATION: Variant of lovD

<400> SEQUENCE: 12

Met Gly Ser Ile Ile Asp Ala Ala Val Ala Ala Asp Pro Val Val Leu
1               5                   10                  15

Met Glu Thr Ala Phe Arg Lys Ala Val Glu Ser Arg Gln Ile Pro Gly

```
            20                  25                  30
Ala Val Ile Met Ala Arg Asp Cys Ser Gly Asn Leu Asn Tyr Thr Arg
        35                  40                  45
Cys Phe Gly Ala Arg Thr Val Arg Arg Asp Glu Cys Asn Gln Leu Pro
    50                  55                  60
Pro Leu Gln Val Asp Thr Pro Cys Arg Leu Ala Ser Ala Thr Lys Leu
65                  70                  75                  80
Leu Thr Thr Ile Met Ala Leu Gln Cys Met Glu Arg Gly Leu Val Asp
                85                  90                  95
Leu Asp Glu Thr Val Asp Arg Leu Leu Pro Asp Leu Ser Ala Met Pro
            100                 105                 110
Val Leu Glu Gly Phe Asp Asp Ala Gly Asn Pro Arg Leu Arg Glu Arg
        115                 120                 125
Arg Gly Lys Ile Thr Leu Arg His Leu Leu Thr His Thr Ser Gly Leu
    130                 135                 140
Ser Tyr Val Phe Leu His Pro Leu Leu Arg Glu Tyr Val Ala Gln Gly
145                 150                 155                 160
His Leu Gln Ser Ala Glu Lys Phe Gly Ile Gln Asn Arg Phe Ala Pro
                165                 170                 175
Pro Leu Val Asn Asp Pro Gly Ala Glu Trp Ile Tyr Gly Ala Ser Ile
            180                 185                 190
Asp Trp Ala Gly Lys Leu Val Glu Arg Ala Thr Gly Leu Asp Leu Glu
        195                 200                 205
Gln Tyr Leu Gln Glu Asn Ile Cys Ala Pro Leu Gly Ile Thr Asp Met
    210                 215                 220
Thr Phe Lys Leu Gln Gln Arg Pro Asp Met Leu Ala Arg Arg Ala Asp
225                 230                 235                 240
Gln Thr His Arg Asn Ser Ser Asp Gly Lys Leu Arg Tyr Asp Asp Ser
                245                 250                 255
Val Tyr Phe Arg Ala Asp Gly Glu Glu Cys Phe Gly Gln Gly Val
            260                 265                 270
Phe Ser Ser Pro Gly Ser Tyr Met Lys Val Leu His Ser Leu Leu Lys
        275                 280                 285
Arg Asp Gly Leu Leu Leu Gln Pro Glu Thr Val Asp Leu Met Phe Gln
    290                 295                 300
Pro Ala Leu Glu Pro Arg Leu Glu Glu Gln Met Asn Gln His Met Asp
305                 310                 315                 320
Ala Ser Pro His Ile Asn Tyr Gly Gly Pro Met Pro Met Val Leu Arg
                325                 330                 335
Arg Ser Phe Gly Leu Gly Gly Ile Ile Ala Leu Glu Asp Leu Asp Gly
            340                 345                 350
Glu Asn Trp Arg Arg Lys Gly Ser Met Thr Phe Gly Gly Pro Asn
        355                 360                 365
Ile Val Trp Gln Ile Asp Pro Lys Ala Gly Leu Cys Thr Leu Val Phe
    370                 375                 380
Phe Gln Leu Glu Pro Trp Asn Asp Pro Val Cys Arg Asp Leu Thr Arg
385                 390                 395                 400
Thr Phe Glu His Ala Ile Tyr Ala Gln Tyr Gln Gln Gly
                405                 410

<210> SEQ ID NO 13
<211> LENGTH: 1242
<212> TYPE: DNA
<213> ORGANISM: Artificial Sequence
```

<220> FEATURE:
<223> OTHER INFORMATION: Variant of lovD

<400> SEQUENCE: 13

```
atgggttcta tcattgatgc ggctgtggcc gcggacccgg tggttctgat ggaaacggct      60
ttccgtaaag cggttgaaag ccgccagatt ccgggtgctg ttattatggc gcgtgattgt     120
agtggtcgtc tgaactacac tcgctgtttc ggcgcacgca ctgtgcgtcg cgacgagtgc     180
aatcaattac caccgctgca ggtggataca ccatgtcgtc tggcaagcgc tactaaatta     240
ctgaccacga ttatggcact gcagtgcatg aacgcggcc tggtagactt ggatgaaact      300
gttgaccgcc tgctgccgga cctgagcgcg atgccggtgc tggaaggctt tgatgatgcc     360
ggcaacccgc gtctgcgcga acgccgtggt aaaattacgt tacgccatct gctgacacac     420
accagcggtc tgtcgtacgt cttcctgcat ccgctgctgc gcgagtatgt tgcccagggt     480
catttgcagg gcgctgagaa gtttggcatt cagaatcgtt ttgcgccgcc attagttaat     540
gatccaggcg cggaatggat ttatggcgct ggcatcgact gggcaggcaa attagtggaa     600
cgcgcaacgg gcttggacct ggaacagtac ttgcaggaga catttgcgc gccgctgggc     660
atcactgata tgacgttcaa actgcagcag cgtccggata tgctggcacg tcgtgccgac     720
atgacccacc gcaactccag cgatggtaaa ctgcgctatg atgactctgt gtattttcgc     780
gcggacggtg aagagtgttt cggggccag ggcgtgttca gcagtccagg cagttacatg      840
aaggttctgc actctctgct gaaacgtgac ggcctgttgc tgcagccaga accgtggat     900
ctgatgttcc agccggcgct ggaaccgcgc ttggaagaac aaatgaacca gcatatggac     960
gcgtcgccgc acatcaacta tggcggtcca atgcctatgg tcctgcgtcg cagcttcggc    1020
ctgggtggta tcattgcact ggaggatctg gatggtgaga actggcgtcg taaaggctcg    1080
atgacgtttg gtggcggtcc aaacattatt tggcagattg acccgaaagc gggtctgtgt    1140
actttagtct ttttccagct ggaaccgtgg aacgacccgg tgtgtcgtga cctgactcgc    1200
accttgaga aagcgatcta tgcacagtat caacagggct aa                        1242
```

<210> SEQ ID NO 14
<211> LENGTH: 413
<212> TYPE: PRT
<213> ORGANISM: Artificial Sequence
<220> FEATURE:
<223> OTHER INFORMATION: Variant of lovD

<400> SEQUENCE: 14

```
Met Gly Ser Ile Ile Asp Ala Ala Val Ala Ala Asp Pro Val Val Leu
1               5                   10                  15

Met Glu Thr Ala Phe Arg Lys Ala Val Glu Ser Arg Gln Ile Pro Gly
            20                  25                  30

Ala Val Ile Met Ala Arg Asp Cys Ser Gly Arg Leu Asn Tyr Thr Arg
        35                  40                  45

Cys Phe Gly Ala Arg Thr Val Arg Arg Asp Glu Cys Asn Gln Leu Pro
    50                  55                  60

Pro Leu Gln Val Asp Thr Pro Cys Arg Leu Ala Ser Ala Thr Lys Leu
65                  70                  75                  80

Leu Thr Thr Ile Met Ala Leu Gln Cys Met Glu Arg Gly Leu Val Asp
                85                  90                  95

Leu Asp Glu Thr Val Asp Arg Leu Leu Pro Asp Leu Ser Ala Met Pro
            100                 105                 110

Val Leu Glu Gly Phe Asp Asp Ala Gly Asn Pro Arg Leu Arg Glu Arg
```

| | | | | | | | | | | | |
|---|---|---|---|---|---|---|---|---|---|---|---|
| | | | 115 | | | | 120 | | | | 125 |

Arg Gly Lys Ile Thr Leu Arg His Leu Leu Thr His Thr Ser Gly Leu
    130                      135                    140

Ser Tyr Val Phe Leu His Pro Leu Leu Arg Glu Tyr Val Ala Gln Gly
145                    150                    155                    160

His Leu Gln Gly Ala Glu Lys Phe Gly Ile Gln Asn Arg Phe Ala Pro
                165                    170                    175

Pro Leu Val Asn Asp Pro Gly Ala Glu Trp Ile Tyr Gly Ala Gly Ile
            180                    185                    190

Asp Trp Ala Gly Lys Leu Val Glu Arg Ala Thr Gly Leu Asp Leu Glu
            195                    200                    205

Gln Tyr Leu Gln Glu Asn Ile Cys Ala Pro Leu Gly Ile Thr Asp Met
210                    215                    220

Thr Phe Lys Leu Gln Gln Arg Pro Asp Met Leu Ala Arg Arg Ala Asp
225                    230                    235                    240

Met Thr His Arg Asn Ser Ser Asp Gly Lys Leu Arg Tyr Asp Asp Ser
                245                    250                    255

Val Tyr Phe Arg Ala Asp Gly Glu Glu Cys Phe Gly Gly Gln Gly Val
            260                    265                    270

Phe Ser Ser Pro Gly Ser Tyr Met Lys Val Leu His Ser Leu Leu Lys
            275                    280                    285

Arg Asp Gly Leu Leu Leu Gln Pro Glu Thr Val Asp Leu Met Phe Gln
            290                    295                    300

Pro Ala Leu Glu Pro Arg Leu Glu Glu Gln Met Asn Gln His Met Asp
305                    310                    315                    320

Ala Ser Pro His Ile Asn Tyr Gly Gly Pro Met Pro Met Val Leu Arg
                325                    330                    335

Arg Ser Phe Gly Leu Gly Gly Ile Ile Ala Leu Glu Asp Leu Asp Gly
            340                    345                    350

Glu Asn Trp Arg Arg Lys Gly Ser Met Thr Phe Gly Gly Gly Pro Asn
                355                    360                    365

Ile Ile Trp Gln Ile Asp Pro Lys Ala Gly Leu Cys Thr Leu Val Phe
            370                    375                    380

Phe Gln Leu Glu Pro Trp Asn Asp Pro Val Cys Arg Asp Leu Thr Arg
385                    390                    395                    400

Thr Phe Glu Lys Ala Ile Tyr Ala Gln Tyr Gln Gln Gly
                405                    410

```
<210> SEQ ID NO 15
<211> LENGTH: 1242
<212> TYPE: DNA
<213> ORGANISM: Artificial Sequence
<220> FEATURE:
<223> OTHER INFORMATION: Variant of lovD

<400> SEQUENCE: 15
atgggttcta tcattgatgc ggctgtggcc gcggacccgg tggttctgat ggaaacggct      60
ttccgtaaag cggttgaaag ccgccagatt ccgggtgctg ttattatggc gcgtgattgt     120
agcggtcgtc tgaactacac tcgctgtttc ggcgcacgca ctgtgcgtcg cgacgagtgc     180
aatcaattac accgctgca ggtggataca ccatgtcgtc tggcaagcgc tactaaatta     240
ctgaccacga ttatggcact gcagtgcatg gaacgcggcc tggtagactt ggatgaaact     300
gttgaccgcc tgctgccgga cctgagcgcg atgccggtgc tggaaggctt tgatgatgcc     360
ggcaacccgc gtctgcgcga acgccgtggt aaaattacgt tacgccatct gctgacacac     420
```

```
accagcggtc tgtcgtacgt cttcctgcat ccgctgctgc gcgagtatgt tgcccagggt    480
catttgcagg gcgctgagaa gtttggcatt cagaatcgtt ttgcgccgcc attagttaat    540
gatccaggcg cggaatggat ttatggcgct ggcatcgact gggcaggcaa attagtggaa    600
cgcgcaacgg gcttggacct ggaacagtac ttgcaggaga catttgcgc gccgctgggc     660 atcactgata tgacgttcaa actgcagcag cgcccggata tgctggcacg tcgtgccgac    720
atgacccacc gcaactccag cgatggtaaa ctgcgctatg atgacacggt gtattttcgc    780
gttgacggtg aagagtgttt cgggggccag ggcgtgttca gcagtccagg cagttacatg    840
aaggttctgc actctctgct gaaacgtgac ggcctgttgc tgcagccagg accgtggat     900 ctgatgttcc agccggcgct ggaaccgcgc ttggaagaac aaatgaacca gcatatggac    960
gcgtcgccgc acatcaacta tggcggtcca atgcctatgg tcctgcgtcg cagcttcggc   1020
ctgggtggta tcattgcact ggaggatctg gatggtgaga actggcgtcg taaaggctcg   1080
atgacgtttg gtggcggtcc aaacattatt tggcagattg acccgaaagc gggtctgtgt   1140
actttagtct ttttccagct ggaaccgtgg agtgacccgg tgtgtcgtga cctgactcgc   1200 accttttgaga aagcgatcta tgcacagtat caacagggct aa                     1242
```

<210> SEQ ID NO 16
<211> LENGTH: 413
<212> TYPE: PRT
<213> ORGANISM: Artificial Sequence
<220> FEATURE:
<223> OTHER INFORMATION: Variant of lovD

<400> SEQUENCE: 16

```
Met Gly Ser Ile Ile Asp Ala Ala Val Ala Ala Asp Pro Val Val Leu
1               5                   10                  15

Met Glu Thr Ala Phe Arg Lys Ala Val Glu Ser Arg Gln Ile Pro Gly
            20                  25                  30

Ala Val Ile Met Ala Arg Asp Cys Ser Gly Arg Leu Asn Tyr Thr Arg
        35                  40                  45

Cys Phe Gly Ala Arg Thr Val Arg Arg Asp Glu Cys Asn Gln Leu Pro
    50                  55                  60

Pro Leu Gln Val Asp Thr Pro Cys Arg Leu Ala Ser Ala Thr Lys Leu
65                  70                  75                  80

Leu Thr Thr Ile Met Ala Leu Gln Cys Met Glu Arg Gly Leu Val Asp
                85                  90                  95

Leu Asp Glu Thr Val Asp Arg Leu Leu Pro Asp Leu Ser Ala Met Pro
            100                 105                 110

Val Leu Glu Gly Phe Asp Asp Ala Gly Asn Pro Arg Leu Arg Glu Arg
        115                 120                 125

Arg Gly Lys Ile Thr Leu Arg His Leu Leu Thr His Thr Ser Gly Leu
    130                 135                 140

Ser Tyr Val Phe Leu His Pro Leu Leu Arg Glu Tyr Val Ala Gln Gly
145                 150                 155                 160

His Leu Gln Gly Ala Glu Lys Phe Gly Ile Gln Asn Arg Phe Ala Pro
                165                 170                 175

Pro Leu Val Asn Asp Pro Gly Ala Glu Trp Ile Tyr Gly Ala Gly Ile
            180                 185                 190

Asp Trp Ala Gly Lys Leu Val Glu Arg Ala Thr Gly Leu Asp Leu Glu
        195                 200                 205

Gln Tyr Leu Gln Glu Asn Ile Cys Ala Pro Leu Gly Ile Thr Asp Met
```

```
                        210               215                   220
Thr Phe Lys Leu Gln Gln Arg Pro Asp Met Leu Ala Arg Arg Ala Asp
225                 230                 235                 240

Met Thr His Arg Asn Ser Ser Asp Gly Lys Leu Arg Tyr Asp Asp Thr
                245                 250                 255

Val Tyr Phe Arg Val Asp Gly Glu Glu Cys Phe Gly Gly Gln Gly Val
            260                 265                 270

Phe Ser Ser Pro Gly Ser Tyr Met Lys Val Leu His Ser Leu Leu Lys
        275                 280                 285

Arg Asp Gly Leu Leu Leu Gln Pro Gly Thr Val Asp Leu Met Phe Gln
290                 295                 300

Pro Ala Leu Glu Pro Arg Leu Glu Glu Gln Met Asn Gln His Met Asp
305                 310                 315                 320

Ala Ser Pro His Ile Asn Tyr Gly Gly Pro Met Pro Met Val Leu Arg
                325                 330                 335

Arg Ser Phe Gly Leu Gly Gly Ile Ile Ala Leu Glu Asp Leu Asp Gly
            340                 345                 350

Glu Asn Trp Arg Arg Lys Gly Ser Met Thr Phe Gly Gly Gly Pro Asn
        355                 360                 365

Ile Ile Trp Gln Ile Asp Pro Lys Ala Gly Leu Cys Thr Leu Val Phe
370                 375                 380

Phe Gln Leu Glu Pro Trp Ser Asp Pro Val Cys Arg Asp Leu Thr Arg
385                 390                 395                 400

Thr Phe Glu Lys Ala Ile Tyr Ala Gln Tyr Gln Gln Gly
                405                 410

<210> SEQ ID NO 17
<211> LENGTH: 1242
<212> TYPE: DNA
<213> ORGANISM: Artificial Sequence
<220> FEATURE:
<223> OTHER INFORMATION: Variant of lovD

<400> SEQUENCE: 17
atgggttcta acattgatgc ggctgtggcc gcggacccgg tggttctgat ggaaacggct    60
ttccgtaaag cggttgaaag ctctcagatt ccgggtgctg ttattatggc gcgtgattgt   120
agcggtcgtc tgaactacac tcgctgtttc ggcgcacgca ctgtgcgtcg cgacgagtgc   180
aatcaattac accgctgcag gtggatacac ccatgtcgtc tggcaagcgc tactaaatta   240
ctgaccacga ttatggcact gcagtgcatg aacgcggcc tggtagactt ggatgaaact   300
gttgaccgcc tgctgccgga cctgagcgcg atgccggtgc tggaaggctt tgatgatgcc   360
ggcaacccgc gtctgcgcga acgcgtggt aaaattacgt tacgccatct gctgacacac   420
accagcggtc tgtcgtacgt cttcctgcat ccgctgctgc gcgagtatgt tgcccagggt   480
catttgcagg cgctgagaa gtttggcatt cagaatcgtt ttgcgccgcc attagttaat   540
gatccaggcg cggaatggat ttatggcgct ggcatcgact gggcaggcaa attagtggaa   600
cgcgcaacgg gcttggacct ggaacagtac ttgcaggaga catttgcgc gccgctgggc   660 atcactgata tgacgttcaa actgcagcag cgcccggata tgctggcacg tcgtgccgac   720
atgacccacc gcaactccag cgatggtaaa ctgcgctatg atgacacggt gtattttcgc   780
catgacggtg aagagtgttt cggggggcag ggcgtgttca gcagtccagg cagttacatg   840
aaggttctgc actctctgct gaaacgtgac ggcctgttgc tgcagccagg accgtggat   900 ctgatgttcc agccggcgct ggaaccgcgt ttggaagaac aaatgaacca gcatatggac   960
```

```
gcgtcgccgc acatcaacta tggcggtcca atgcctatgg tcctgcgtcg cagcttcggc    1020
ctgggtggta tcattgcact ggaggatctg gatggtgaga actggcgtcg taaaggctcg    1080
atgacgtttg gtggcggtcc aaacattatt tggcagattg acccgaaagc gggtctgtgt    1140
actttagtct ttttccagct ggaaccgtgg agtgacccgg tgtgtcgtga cctgactcgc    1200
accttggaga aagcgatcta tgcacagtat caacagggct aa                      1242
```

<210> SEQ ID NO 18
<211> LENGTH: 413
<212> TYPE: PRT
<213> ORGANISM: Artificial Sequence
<220> FEATURE:
<223> OTHER INFORMATION: Variant of lovD

<400> SEQUENCE: 18

```
Met Gly Ser Asn Ile Asp Ala Ala Val Ala Ala Asp Pro Val Val Leu
1               5                   10                  15

Met Glu Thr Ala Phe Arg Lys Ala Val Glu Ser Ser Gln Ile Pro Gly
            20                  25                  30

Ala Val Ile Met Ala Arg Asp Cys Ser Gly Arg Leu Asn Tyr Thr Arg
        35                  40                  45

Cys Phe Gly Ala Arg Thr Val Arg Arg Asp Glu Cys Asn Gln Leu Pro
    50                  55                  60

Pro Leu Gln Val Asp Thr Pro Cys Arg Leu Ala Ser Ala Thr Lys Leu
65                  70                  75                  80

Leu Thr Thr Ile Met Ala Leu Gln Cys Met Glu Arg Gly Leu Val Asp
                85                  90                  95

Leu Asp Glu Thr Val Asp Arg Leu Leu Pro Asp Leu Ser Ala Met Pro
            100                 105                 110

Val Leu Glu Gly Phe Asp Asp Ala Gly Asn Pro Arg Leu Arg Glu Arg
        115                 120                 125

Arg Gly Lys Ile Thr Leu Arg His Leu Leu Thr His Thr Ser Gly Leu
    130                 135                 140

Ser Tyr Val Phe Leu His Pro Leu Leu Arg Glu Tyr Val Ala Gln Gly
145                 150                 155                 160

His Leu Gln Gly Ala Glu Lys Phe Gly Ile Gln Asn Arg Phe Ala Pro
                165                 170                 175

Pro Leu Val Asn Asp Pro Gly Ala Glu Trp Ile Tyr Gly Ala Gly Ile
            180                 185                 190

Asp Trp Ala Gly Lys Leu Val Glu Arg Ala Thr Gly Leu Asp Leu Glu
        195                 200                 205

Gln Tyr Leu Gln Glu Asn Ile Cys Ala Pro Leu Gly Ile Thr Asp Met
    210                 215                 220

Thr Phe Lys Leu Gln Gln Arg Pro Asp Met Leu Ala Arg Arg Ala Asp
225                 230                 235                 240

Met Thr His Arg Asn Ser Ser Asp Gly Lys Leu Arg Tyr Asp Asp Thr
                245                 250                 255

Val Tyr Phe Arg His Asp Gly Glu Glu Cys Phe Gly Gly Gln Gly Val
            260                 265                 270

Phe Ser Ser Pro Gly Ser Tyr Met Lys Val Leu His Ser Leu Leu Lys
        275                 280                 285

Arg Asp Gly Leu Leu Leu Gln Pro Gly Thr Val Asp Leu Met Phe Gln
    290                 295                 300

Pro Ala Leu Glu Pro Arg Leu Glu Glu Gln Met Asn Gln His Met Asp
```

```
                        305                 310                 315                 320
Ala Ser Pro His Ile Asn Tyr Gly Gly Pro Met Pro Met Val Leu Arg
                        325                 330                 335

Arg Ser Phe Gly Leu Gly Gly Ile Ile Ala Leu Glu Asp Leu Asp Gly
                        340                 345                 350

Glu Asn Trp Arg Arg Lys Gly Ser Met Thr Phe Gly Gly Gly Pro Asn
                        355                 360                 365

Ile Ile Trp Gln Ile Asp Pro Lys Ala Gly Leu Cys Thr Leu Val Phe
                370                 375                 380

Phe Gln Leu Glu Pro Trp Ser Asp Pro Val Cys Arg Asp Leu Thr Arg
385                 390                 395                 400

Thr Phe Glu Lys Ala Ile Tyr Ala Gln Tyr Gln Gln Gly
                        405                 410

<210> SEQ ID NO 19
<211> LENGTH: 1242
<212> TYPE: DNA
<213> ORGANISM: Artificial Sequence
<220> FEATURE:
<223> OTHER INFORMATION: Variant of lovD

<400> SEQUENCE: 19
atgggttcta acattgatgc ggctgtggcc gcggacccgg tggttctgat ggaaacggct      60
ttccgtaaag cggttgaaag ctctcagatt ccgggtgctg ttttgatggc gcgtgattgt     120
agcggtcgtc tgaactacac tcgctgtttc ggcgcacgca ctgtgcgtcg cgacgagtgc     180
aatcaattac accgctgcag gtggatacac ccatgtcgtc tggcaagcgc tactaaatta     240
ctgaccacga ttatggcact gcagtgcatg aacgcggcc tggtacgctt ggatgaaact      300
gttgaccgcc tgctgccgga cctgtgcgcg atgccggtgc tggaaggctt tgatgatgcc     360
ggcaacccgc gtctgcgcga acgccgtggt aaaattacgt tacgccatct gctgacacac     420
accagcggtc tgtcgtacgt cttcctgcat ccgctgctgc gcgagtatgt tgcccagggt     480
catttgcagg gcgctgagaa gtttggcatt cagaatcgtt ttgcgccgcc attagttaat     540
gatccaggcg cggaatggat ttatggcgct ggcatcgact gggcaggcaa attagtggaa     600
cgcgcaacgg gcttggacct ggaacagtac ttgcaggaga catttgcgc gccgctgggc      660
atcactgata tgacgttcaa actgcagcag cgccccggata tgctggcacg tcgtgccgac    720
atgacccacc gcaactccag cgatggtaaa ctgcgctatg atgacacggt gtattttcgc     780
catgacggtg aagagtgttt cggggggccag ggcgtgttca gcagtccagg cagttacatg    840
aaggttctgc actctctgct gaaacgtgac ggcctgttgc tgcagccagg accgtggat      900
ctgatgttcc agccggcgct ggaaccgcgt ttggaagaac aaatgaacca gcatatggac     960
gcgtcgccgc acatcaacta tggcggtcca atgcctatgg tcatgcgtcg cagcttcggc    1020
ctgggtggta tcattgcact ggaggatctg gatggtgaga ctggcgtcg taaaggctcg    1080
atgacgtttg gtggcggtcc aaacattatt tggcagattg acccgaaagc gggtctgtgt   1140
actttagtct ttttccagct ggaaccgtgg agtgacccgg tgtgtcgtga cctgactcgc   1200
acctttgaga aagcgatcta tgcacagtat caacagggct aa                       1242

<210> SEQ ID NO 20
<211> LENGTH: 413
<212> TYPE: PRT
<213> ORGANISM: Artificial Sequence
<220> FEATURE:
<223> OTHER INFORMATION: Variant of lovD
```

<400> SEQUENCE: 20

```
Met Gly Ser Asn Ile Asp Ala Ala Val Ala Asp Pro Val Val Leu
1               5                   10                  15

Met Glu Thr Ala Phe Arg Lys Ala Val Glu Ser Ser Gln Ile Pro Gly
            20                  25                  30

Ala Val Leu Met Ala Arg Asp Cys Ser Gly Arg Leu Asn Tyr Thr Arg
                35                  40                  45

Cys Phe Gly Ala Arg Thr Val Arg Arg Asp Glu Cys Asn Gln Leu Pro
    50                  55                  60

Pro Leu Gln Val Asp Thr Pro Cys Arg Leu Ala Ser Ala Thr Lys Leu
65                  70                  75                  80

Leu Thr Thr Ile Met Ala Leu Gln Cys Met Glu Arg Gly Leu Val Arg
                    85                  90                  95

Leu Asp Glu Thr Val Asp Arg Leu Leu Pro Asp Leu Cys Ala Met Pro
                100                 105                 110

Val Leu Glu Gly Phe Asp Asp Ala Gly Asn Pro Arg Leu Arg Glu Arg
                115                 120                 125

Arg Gly Lys Ile Thr Leu Arg His Leu Leu Thr His Thr Ser Gly Leu
    130                 135                 140

Ser Tyr Val Phe Leu His Pro Leu Leu Arg Glu Tyr Val Ala Gln Gly
145                 150                 155                 160

His Leu Gln Gly Ala Glu Lys Phe Gly Ile Gln Asn Arg Phe Ala Pro
                    165                 170                 175

Pro Leu Val Asn Asp Pro Gly Ala Glu Trp Ile Tyr Gly Ala Gly Ile
                180                 185                 190

Asp Trp Ala Gly Lys Leu Val Glu Arg Ala Thr Gly Leu Asp Leu Glu
            195                 200                 205

Gln Tyr Leu Gln Glu Asn Ile Cys Ala Pro Leu Gly Ile Thr Asp Met
210                 215                 220

Thr Phe Lys Leu Gln Gln Arg Pro Asp Met Leu Ala Arg Arg Ala Asp
225                 230                 235                 240

Met Thr His Arg Asn Ser Ser Asp Gly Lys Leu Arg Tyr Asp Asp Thr
                245                 250                 255

Val Tyr Phe Arg His Asp Gly Glu Glu Cys Phe Gly Gly Gln Gly Val
                260                 265                 270

Phe Ser Ser Pro Gly Ser Tyr Met Lys Val Leu His Ser Leu Leu Lys
            275                 280                 285

Arg Asp Gly Leu Leu Leu Gln Pro Gly Thr Val Asp Leu Met Phe Gln
290                 295                 300

Pro Ala Leu Glu Pro Arg Leu Glu Glu Gln Met Asn Gln His Met Asp
305                 310                 315                 320

Ala Ser Pro His Ile Asn Tyr Gly Gly Pro Met Pro Met Val Met Arg
                325                 330                 335

Arg Ser Phe Gly Leu Gly Gly Ile Ile Ala Leu Glu Asp Leu Asp Gly
                340                 345                 350

Glu Asn Trp Arg Arg Lys Gly Ser Met Thr Phe Gly Gly Pro Asn
            355                 360                 365

Ile Ile Trp Gln Ile Asp Pro Lys Ala Gly Leu Cys Thr Leu Val Phe
    370                 375                 380

Phe Gln Leu Glu Pro Trp Ser Asp Pro Val Cys Arg Asp Leu Thr Arg
385                 390                 395                 400
```

```
Thr Phe Glu Lys Ala Ile Tyr Ala Gln Tyr Gln Gln Gly
            405                 410
```